(12) United States Patent
Yacoubian et al.

(10) Patent No.: US 7,919,262 B2
(45) Date of Patent: Apr. 5, 2011

(54) 14-3-3 PROTEINS FOR DIAGNOSIS OF PARKINSON'S DISEASE

(75) Inventors: Talene Alene Yacoubian, Birmingham, AL (US); David G. Standaert, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 12/267,337

(22) Filed: Nov. 7, 2008

(65) Prior Publication Data

US 2009/0186365 A1    Jul. 23, 2009

Related U.S. Application Data

(60) Provisional application No. 60/986,128, filed on Nov. 7, 2007.

(51) Int. Cl.
*G01N 33/53* (2006.01)
*G01N 33/567* (2006.01)

(52) U.S. Cl. ......... 435/7.1; 435/7.21; 435/7.8; 435/7.92

(58) Field of Classification Search ........................ None
See application file for complete search history.

(56) References Cited

U.S. PATENT DOCUMENTS

| 5,856,445 | A | 1/1999 | Korsmeyer |
| 5,998,149 | A | 12/1999 | Hsich et al. |
| 7,001,720 | B1 | 2/2006 | Polymeropoulous et al. |
| 2005/0009094 | A1 | 1/2005 | Mueller et al. |

OTHER PUBLICATIONS

Kevin Welch & Junying Yuan, Releasing the Nerve Cell Killers, Nature Medicine, vol. 8 No. 6, Nature Publishing Group, Jun. 2002.
Jin Xu, Shyan-Yuan Kao, Frank J.S. Lee Weihong Song, Lee-Way Jin & Bruce Yankner, Dopamine-dependant neurotoxicity of α-synuclein: A mechanism for selective neurodegeneration in Parkinson disease, Nature Medicine, vol. 8 No. 6, Nature Publishing Group, Jun. 2002.
Nahum Meller, Yun-Cai Liu, Tassie L. Collins, Nathalie Bonnefoy-Berard, Gottfried Baier, Noah Isakov and Amnon Altman, Direct Interaction Between Protein Kinase Cθ (PKCθ) and 14-3- 3τ in T cells: 14-3-3 Overexpression Results in Inhibition of PKC θ Translocation and Function†, Molecular and Cell. Biology, Oct. 1996, p. 5782-5791, vol. 16, No. 10, American Society for Microbiology, 1996.
John A. Thorson,1 Lily W. K. Yu,1 Alice L. Hsu,1 Neng-Yao Shih,1 Paul R. Graves,2 J. William Tanner,1 Paul M. Allen,1 Helen Piwnica-Worms,2,3 and Andrey S. Shaw1,*, 14-3-3 Proteins Are Required for Maintenance of Raf-1 Phosphorylation and Kinase Activity, Molecular and Cell. Biology, Sep. 1998, p. 5229-5238, vol. 18, No. 9, American Society for Microbiology, 1998.
Gary R. Fanger, Christian Widmann, Amy C. Porter , Sue Sather, Gary L. Johnson, and Richard R. Vaillancourt, 14-3-3 Proteins Interact with Specific MEK Kinases, The Journal of Biological Chemistry, vol. 273, Issue 6, 3476-3483, Feb. 6, 1998.
S. C. Masters, R. R. Subramanian, A. Truong, H. Yang, K. Fujii, H. Zhang, H. Fu, Survival-promoting functions of 14-3-3 proteins. Biochemical Society Transactions (2002) vol. 30, part 4.
Masaya Nomura, Shigeomi Shimizu, Tomoyasu Sugiyama, Masashi Narita, Toshinori Ito, Hikaru Matsuda, and Yoshihide Tsujimoto; 14-3-3 Interacts Directly with and Negatively Regulates Proapoptotic Bax*, The Journal of Biological Chemistry, vol. 278, Issue 3, 2058-2065, Jan. 17, 2003.
Michele K. Dougherty and Deborah K. Morrison, Unlocking the code of 14-3-3, Journal of Cell Science 117, 1875-1884 (2004), Published by The Company of Biologists 2004.
Pierre-Olivier Fernagut and Marie-Francoise Chesselet , Alpha-synuclein and transgenic mouse models, Neurobiology of Disease, vol. 17, Issue 2, Nov. 2004, pp. 123-130.
Elizabeth J. Ryu, James M. Angelastro, and Lloyd A. Greene, Analysis of gene expression changes in a cellular model of Parkinson disease, Neurobiology of Disease, vol. 18, Issue 1, Feb. 2005, pp. 54-74.
William Lin, B.A., Un Jung Kang, MD, Neuroprotective Therapy in Parkinson's Disease: Current Status and New Directions from Experimental and Genetic Clues, Journal of Clinical Neurology, vol. 1, Oct. 2005.
Shigeto Sato, Tomoki Chiba, Eri Sakata, Koichi Kato, Yoshikuni Mizuno, Nobutaka Hattori and Keiji Tanaka, 14-3-3 is a novel regulator of parkin ubiquitin ligase, The EMBO Journal (2006) 25, 211-221, doi:10.1038/sj.emboj.7600774, Published online Aug. 11, 2005.
Luca Brunelli, Katarzyna A. Cieslik, Joseph L. Alcorn, Matteo Vatta, Antonio Baldini, Peroxisome Proliferator-Activated Receptor-δ Upregulates 14-3-3 in Human Endothelial Cells via CCAAT/Enhancer Binding Protein-β, Circulation Research. 2007;100:e59-e71, American Heart Association, Inc. 2007.

*Primary Examiner* — Olga N Chernyshev
(74) *Attorney, Agent, or Firm* — Bradley Arant Boult Cummings, LLP

(57) ABSTRACT

The present disclosure is directed to methods for treatment and prevention of disease states characterized by a decreased 14-3-3 polypeptide expression or activity. In one embodiment, the present disclosure provides methods for the treatment and/or prevention of Parkinson's disease, neurodegeneration and/or diseases characterized, at least in part, by neurodegeneration, by increasing a 14-3-3 polypeptide activity.

1 Claim, 10 Drawing Sheets

FIG. 1A (SEQ ID NO: 1)
MTMDKSELVQKAKLAEQAERYDDMAAAMKAVTEQGHELSNEERNLLSVAYKNVVGARRSS
WRVISSIEQKTERNEKKQQMGKEYREKIEAELQDICNDVLELLDKYLIPNATQPESKVFY
LKMKGDYFRYLSEVASGDNKQTTVSNSQQAYQEAFEISKKEMQPTHPIRLGLALNFSVFY
YEILNSPEKACSLAKTAFDEAIAELDTLNEESYKDSTLIMQLLRDNLTLWTSENQGDEGD
AGEGEN

FIG. 1B (SEQ ID NO: 2)
MVDREQLVQKARLAEQAERYDDMAAAMKNVTELNEPLSNEERNLLSVAYKNVVGARRSSW
RVISSIEQKTSADGNEKKIEMVRAYREKIEKELEAVCQDVLSLLDNYLIKNCSETQYESK
VFYLKMKGDYYRYLAEVATGEKRATVVESSEKAYSEAHEISKEHMQPTHPIRLGLALNYS
VFYYEIQNAPEQACHLAKTAFDDAIAELDTLNEDSYKDSTLIMQLLRDNLTLWTSDQQDD
DGGEGNN

FIG. 1C (SEQ ID NO: 3)
MDDREDLVYQAKLAEQAERYDEMVESMKKVAGMDVELTVEERNLLSVAYKNVIGARRASW
RIISSIEQKEENKGGEDKLKMIREYRQMVETELKLICCDILDVLDKHLIPAANTGESKVF
YYKMKGDYHRYLAEFATGNDRKEAAENSLVAYKAASDIAMTELPPTHPIRLGLALNFSVF
YYEILNSPDRACRLAKAAFDDAIAELDTLSEESYKDSTLIMQLLRDNLTLWTSDMQGDGE
EQNKEALQDVEDENQ

FIG. 1D (SEQ ID NO: 4)
MDKNELVQKAKLAEQAERYDDMAACMKSVTEQGAELSNEERNLLSVAYKNVVGARRSSWR
VVSSIEQKTEGAEKKQQMAREYREKIETELRDICNDVLSLLEKFLIPNASQAESKVFYLK
MKGDYYRYLAEVAAGDDKKGIVDQSQQAYQEAFEISKKEMQPTHPIRLGLALNFSVFYYE
ILNSPEKACSLAKTAFDEAIAELDTLSEESYKDSTLIMQLLRDNLTLWTSDTQGDEAEAG
EGGEN

FIG. 1E (SEQ ID NO: 5)
MGDREQLLQRARLAEQAERYDDMASAMKAVTELNEPLSNEDRNLLSVAYKNVVGARRSSW
RVISSIEQKTMADGNEKKLEKVKAYREKIEKELETVCNDVLSLLDKFLIKNCNDFQYESK
VFYLKMKGDYYRYLAEVASGEKKNSVVEASEAAYKEAFEISKEQMQPTHPIRLGLALNFS
VFYYEIQNAPEQACLLAKQAFDDAIAELDTLNEDSYKDSTLIMQLLRDNLTLWTSDQQDE
EAGEGN

FIG. 1F (SEQ ID NO: 6)
MEKTELIQKAKLAEQAERYDDMATCMKAVTEQGAELSNEERNLLSVAYKNVVGGRRSAWR
VISSIEQKTDTSDKKLQLIKDYREKVESELRSICTTVLELLDKYLIANATNPESKVFYLK
MKGDYFRYLAEVACGDDRKQTIDNSQGAYQEAFDISKKEMQPTHPIRLGLALNFSVFYYE
ILNNPELACTLAKTAFDEAIAELDTLNEDSYKDSTLIMQLLRDNLTLWTSDSAGEECDAA
EGAEN a.

b.

6a.

b.

a.

b.

c.

d.

e.

f.

*p<0.05
**p<0.005

SEQUENCE LISTING

<160> NUMBER OF SEQ ID NOS: 25

<210> SEQ ID NO 1
<211> LENGTH: 246
<212> TYPE: PRT
<213> ORGANISM: Homo sapiens

<400> SEQUENCE: 1

```
Met Thr Met Asp Lys Ser Glu Leu Val Gln Lys Ala Lys Leu Ala Glu
1               5                   10                  15

Gln Ala Glu Arg Tyr Asp Asp Met Ala Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly Glu Gly Glu Asn
                245
```

<210> SEQ ID NO 2
<211> LENGTH: 247
<212> TYPE: PRT
<213> ORGANISM: Homo sapiens

<400> SEQUENCE: 2

```
Met Val Asp Arg Glu Gln Leu Val Gln Lys Ala Arg Leu Ala Glu Gln
1               5                   10                  15

Ala Glu Arg Tyr Asp Asp Met Ala Ala Met Lys Asn Val Thr Glu
            20                  25                  30

Leu Asn Glu Pro Leu Ser Asn Glu Glu Arg Asn Leu Leu Ser Val Ala
            35                  40                  45

Tyr Lys Asn Val Val Gly Ala Arg Arg Ser Ser Trp Arg Val Ile Ser
50                  55                  60

Ser Ile Glu Gln Lys Thr Ser Ala Asp Gly Asn Glu Lys Lys Ile Glu
65                  70                  75                  80

Met Val Arg Ala Tyr Arg Glu Lys Ile Glu Lys Glu Leu Glu Ala Val
                85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
                115                 120                 125

Asp Tyr Tyr Arg Tyr Leu Ala Glu Val Ala Thr Gly Glu Lys Arg Ala
130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
                195                 200                 205

Asp Thr Leu Asn Glu Asp Ser Tyr Lys Asp Ser Thr Leu Ile Met Gln
210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245
```

<210> SEQ ID NO 3
<211> LENGTH: 255
<212> TYPE: PRT
<213> ORGANISM: Homo sapiens

<400> SEQUENCE: 3

```
Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
```

```
                    115                 120                 125
His Arg Tyr Leu Ala Glu Phe Ala Thr Gly Asn Asp Arg Lys Glu Ala
130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                    165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
            210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 4
<211> LENGTH: 245
<212> TYPE: PRT
<213> ORGANISM: Homo sapiens

<400> SEQUENCE: 4

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
                20                  25                  30

Gly Ala Glu Leu Ser Asn Glu Glu Arg Asn Leu Leu Ser Val Ala Tyr
            35                  40                  45

Lys Asn Val Val Gly Ala Arg Arg Ser Ser Trp Arg Val Val Ser Ser
50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245
```

<210> SEQ ID NO 5
<211> LENGTH: 246
<212> TYPE: PRT
<213> ORGANISM: Homo sapiens

<400> SEQUENCE: 5

```
Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245
```

<210> SEQ ID NO 6
<211> LENGTH: 245
<212> TYPE: PRT
<213> ORGANISM: Homo sapiens

<400> SEQUENCE: 6

```
Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80
```

```
Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
            115                 120                 125

Leu Ala Glu Val Ala Cys Gly Asp Asp Arg Lys Gln Thr Ile Asp Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
            195                 200                 205

Asp Ser Tyr Lys Asp Ser Thr Leu Ile Met Gln Leu Leu Arg Asp Asn
210                 215                 220

Leu Thr Leu Trp Thr Ser Asp Ser Ala Gly Glu Glu Cys Asp Ala Ala
225                 230                 235                 240

Glu Gly Ala Glu Asn
                245

<210> SEQ ID NO 7
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa can be any naturally occuring amino acid
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MISC_FEATURE
<222> LOCATION: (5)..(5)
<223> OTHER INFORMATION: Xaa can be any naturally occuring amino acid

<400> SEQUENCE: 7

Arg Ser Xaa Ser Xaa Pro
1               5

<210> SEQ ID NO 8
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa can be any naturally occuring amino acid
<220> FEATURE:
<221> NAME/KEY: MISC_FEATURE
<222> LOCATION: (3)..(3)
<223> OTHER INFORMATION: Xaa can be tyrosine or phenylalanine
<220> FEATURE:
<221> NAME/KEY: MISC_FEATURE
<222> LOCATION: (4)..(4)
<223> OTHER INFORMATION: Xaa can be any naturally occuring amino acid
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MISC_FEATURE
```

```
<222> LOCATION: (6)..(6)
<223> OTHER INFORMATION: Xaa can be any naturally occurring amino acid

<400> SEQUENCE: 8

Arg Xaa Xaa Xaa Ser Xaa Pro
1               5

<210> SEQ ID NO 9
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 9
aaaggtcccg tgctcatacc                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 10
gccgcctcaa cacattattc                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 11
ttgggtgtta gcttgaggtg                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 12
gaggagtcgg caagaatgag                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 13
tctgtgtccc gcttgtactg                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 14
aggcaggcac acttctcaac                                           20
```

```
<210> SEQ ID NO 15
<211> LENGTH: 21
<212> TYPE: DNA
<213> ORGANISM: Artificial Sequence
<220> FEATURE:
<223> OTHER INFORMATION: Synthetic PCR primer

<400> SEQUENCE: 15
tctagcaaat ccaggtgatg g                                              21

<210> SEQ ID NO 16
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 16
aggctgatgg tgaaggaatg                                                20

<210> SEQ ID NO 17
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 17
aggagtgaca gcacacttgg                                                20

<210> SEQ ID NO 18
<211> LENGTH: 22
<212> TYPE: DNA
<213> ORGANISM: Artificial Sequence
<220> FEATURE:
<223> OTHER INFORMATION: Synthetic PCR primer

<400> SEQUENCE: 18
gttgcttctg aaaggaaacc tc                                             22

<210> SEQ ID NO 19
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 19
gtctgtcctt catcgcagtc                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 20
tcctcgttgc tcttctgctc                                                20

<210> SEQ ID NO 21
<211> LENGTH: 21
<212> TYPE: DNA
<213> ORGANISM: Artificial Sequence
<220> FEATURE:
<223> OTHER INFORMATION: Synthetic PCR primer
```

```
<400> SEQUENCE: 21
ggctagtgat tggaggaaac c                                                   21

<210> SEQ ID NO 22
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 22
tcatatcgct ctgcctgctc                                                     20

<210> SEQ ID NO 23
<211> LENGTH: 19
<212> TYPE: DNA
<213> ORGANISM: Artificial Sequence
<220> FEATURE:
<223> OTHER INFORMATION: Synthetic PCR primer

<400> SEQUENCE: 23
tggtgaagca ggcatctga                                                      19

<210> SEQ ID NO 24
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 24
tgctgttgaa gtcgcaggag                                                     20

<210> SEQ ID NO 25
<211> LENGTH: 248
<212> TYPE: PRT
<213> ORGANISM: Homo sapiens

<400> SEQUENCE: 25
```

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175

```
Ser Val Phe Tyr Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Glu Ser Tyr Lys Asp Ser Thr Leu Ile Met Gln Leu Leu Arg
    210                 215                 220

Asp Asn Leu Thr Leu Trp Thr Ser Asp Asn Ala Gly Glu Glu Gly Gly
225             230                 235                 240

Glu Ala Pro Gln Glu Pro Gln Ser
                245
```

14-3-3 PROTEINS FOR DIAGNOSIS OF PARKINSON'S DISEASE

This application claims the benefit of U.S. Provisional Application No. 60/986,128, filed Nov. 7, 2007.

FIELD OF THE DISCLOSURE

The present disclosure is directed to methods for treatment and prevention of disease states characterized by a decreased 14-3-3 polypeptide expression or activity, such as, but not limited to, Parkinson's disease, neurodegeneration and/or diseases characterized, at least in part, by neurodegeneration.

BACKGROUND

A number of neurological diseases are characterized by neurodegeneration. For example, Parkinson's disease (PD) is a debilitating neurological disorder marked by tremor, bradykinesia, rigidity and poor balance. PD is associated with the loss of dopaminergic neurons in the brain, particularly in the substantia nigra. Other disease state characterized by neurodegeneration include, but are not limited to, Alexander disease, Alper's disease, Alzheimer's disease, amyotrophic lateral sclerosis, ataxia telangiectasia, Batten disease, bovine spongiform encephalopathy (BSE), Canavan disease, Cockayne syndrome, corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), multiple sclerosis, multiple system atrophy, narcolepsy, neuroborreliosis, Pelizaeus-Merzbacher disease, Pick's disease, primary lateral sclerosis, Refsum's disease, Sandhoff disease and Schilder's disease.

14-3-3 proteins are a family of highly conserved acidic 30-kd proteins found throughout the evolutionary scale, from yeasts to human. There are seven 14-3-3 isoforms in mammals named β, γ, ε, ζ, η, θ (also termed as τ), and σ (Dougherty and Morrison, *J Cell Sci*, 117:1875-84, 2004). Although the 14-3-3 protein is widely distributed in neural and non-neural tissues, it is expressed most abundantly in neurons in the central nervous system (CNS) where it can represent more than 1% of total protein.

These proteins contain five highly conserved regions that are separated by less homologous regions (Gardino, et al. *Semin Cancer Biol* 16, 173-82, 2006). The conserved regions are involved in ligand binding and dimerization (Berg, et al., *Nat Rev Neurosci* 4, 752-62, 2003). The unconserved carboxyl termini probably regulate 14-3-3 function and stabilize the unbound form. Phylogenetic analysis of the different isoforms suggest three subgroups among the isoform: 1) γ and η 2) β, θ, ε and ζ and 3) σ.

These proteins form homo- or heterodimers that lack intrinsic enzymatic activity. As dimers, 14-3-3s form a highly conserved concave amphipathic groove that mediates interactions with ligand. The amphipathic groove is a large cup-like structure with two ligand-binding sites in its groove. The dimeric complex acts as a novel molecular chaperone that interacts with key molecules involved in cell differentiation, proliferation, transformation, and apoptosis (van Hemert M J et al., *Bioessays*; Aitken A, et al., *Biochem Soc Trans*. 2002; 30:351-360; Berg D, et al., *Nature Rev Neurosci*. 2002; 4:752-762). 14-3-3 protein regulates the function of target proteins by restricting their subcellular location, bridging them to modulate catalytic activity, and protecting them from dephosphorylation or proteolysis (Muslin A J, et al., *Cell Signal*. 2000; 12:703-709; Yaffe M B, *FEBS Lett*. 2002; 513:53-57; Tzivion G, et al., *J Biol. Chem*. 2002; 277:3061-3064).

In general, the 14-3-3 protein binds to phosphoserine-containing motifs of the ligands such as RSXpSXP (SEQ ID NO. 7) and RXY/FXpSXP (SEQ ID NO. 8) in a sequence-specific manner (where X is any amino acid and p represents a phosphorylated residue). More than 300 proteins have been identified as being 14-3-3 binding partners. These binding partners participate in a wide range of cellular functions, including primary metabolism, cell proliferation, actin dynamics, proteosomal function, transcription, and apoptosis. In the central nervous system, proposed functional roles for 14-3-3s include neuronal migration during development, learning, and neurodegeneration. The binding partners include a range of intracellular signaling regulators such as Raf, BAD, protein kinase C (PKC), phophatidylinositol 3-kinase (PI3K), and cdc25 phosphatase. Binding of the 14-3-3 protein to Raf is indispensable for Raf kinase activity in the Ras/MAPK signaling pathway, whereas 14-3-3 binding to the mitochondrial Bcl-2 family member BAD, when phosphorylated by a serine/threonine kinase Akt, inhibits apoptosis. In addition to the phosphorylation-dependent interaction, the 14-3-3 protein can interact with a set of target proteins in a phosphorylation-independent manner (Zhai et al., *J Biol Chem*. 2001; 276:41318-411324). The ε isoform binds to p190RhoGEF via a phosphoserine-independent interaction.

Previous studies indicated that the 14-3-3 protein has isoform-specific and nonredundant functions (Broadie K, et al., *Neuron*. 1997; 19:391-402). Synaptic transmission and associative learning are impaired in *Drosophila* mutants lacking the ζ protein. The 14-3-3 isoforms have distinct affinities for their target proteins. A preferential interaction is observed between PKCθ and the human 14-3-3θ isoform in T cells (Meller N, et al., *Mol Cell Biol*. 1996; 16:5782-5791), IGF1-receptor, IRS1, and ε isoform (Craparo A, et al., *J Biol Chem*. 1997; 272:11663-1), the apoptosis-inhibitor A20 and the human β and η isoforms (Vincenz C, et al., *J Biol Chem*. 1996; 271:20029-20034), and glucocorticoid receptor and the human η isoform (Wakui H, et al., *J Biol Chem*. 1997; 272:8153-8156). The human β and ζ isoforms and not γ or ε isoforms interact with phosphorylated tau (Hashiguchi M, et al., *J Biol Chem*. 2000; 275:25247-25254). Furthermore, different isoforms show distinct patterns of spatial, temporal, and subcellular distribution. In the developing rat brain, defined populations of neurons express β, γ, ζ, and θ isoforms at specific stages of development (Watanabe M, et al., *Mol Brain Res*. 1993; 17:135-146, Watanabe M, et al., *Mol Brain Res*. 1994; 25:113-121). In the adult mouse brain, β, γ, η, and ζ isoforms are widely distributed with the localization primarily in neurons, although some glial cells express ε, θ, and ζ isoforms (Baxter H C, et al., *Neuroscience*. 2002; 109:5-14).

Recently, several lines of evidence have indicated that the 14-3-3 protein is involved in neurodegenerative processes. The 14-3-3 protein detected in the cerebrospinal fluid of Creutzfeldt-Jacob disease has been used as a biochemical marker for the premortem diagnosis of Creutzfeldt-Jacob disease in the context of differential diagnosis of progressive dementia. However, recent studies showed that the 14-3-3 protein is occasionally detectable in the cerebrospinal fluid of infectious meningoencephalitis, metabolic encephalopathy, cerebrovascular diseases, and multiple sclerosis presenting with severe myelitis, suggesting that 14-3-3 protein is not a marker specific for prion diseases but for extensive destruction of brain tissues causing the leakage of 14-3-3 protein into the cerebrospinal fluid. In the Alzheimer's disease brain, neurofibrillary tangles express immunoreactivity against the 14-3-3 protein (Layfield R, et al., *Neurosci Lett*. 1996; 209:

57-60). The 14-3-3ζ homodimer interacts with tau and glycogen synthase kinase-3β (GSK3β), and stimulates GSK3β-mediated tau phosphorylation.

In the Parkinson's disease brain and in Dementia with Lewy Bodies, Lewy bodies possess γ, ε, ζ, and θ isoforms that interact with α-synuclein (α-syn) (Berg D, et al., *Ann Neurol.* 2003; 54:135, Ostrerova N, et al., *J Neurosci.* 1999; 19:5782-5791). 14-3-3 proteins have been found in Lewy Bodies in multiple System Atrophy. Dopamine-dependent neurotoxicity is mediated by a soluble complex composed of the 14-3-3 protein and α-synuclein, whose levels are markedly elevated in the substantia nigra of the Parkinson's disease brain (Xu J, et al., *Nat Med.* 2002; 8:600-606). The neurotoxicity of ataxin-1, the causative protein of spinocerebellar ataxia type 1, is enhanced by ε and ζ isoforms that bind to and stabilize ataxin-1 phosphorylated by Akt, thereby slowing its degradation (Chen H-K, et al., *Cell.* 2003; 113:457-468). Finally, expression of the θ isoform is enhanced in the spinal cord of amyotrophic lateral sclerosis (Malaspina A, et al., *J Neurochem.* 2000; 75:2511-2520). However, it remains unknown whether the 14-3-3 protein plays an active role in the pathological process of MS.

14-3-3 proteins share considerable homology with α-syn (Ostreova, N, et al., J Neuroscu, 19:1578-91, 1999) and 14-3-3 proteins can be co-immunoprecipitated with α-syn from mammalian brains (Ostreova, N, et al., J Neuroscu, 19:1578-91, 1999; Xu, J, et al., Nat Med, 8:600-06, 2002). Increased co-immunoprecipitation is observed in the nigra of PD brains (Xu, J, et al., Nat Med, 8:600-06, 2002). In recent studies, the protein α-syn has been discovered to have a central role in the pathogenesis of PD. Families with mutant α-syn exhibit autosomal dominant PD (Athanassiadou, A, et al., Am J Hum Genet, 66:555-08, 1999; Kruger, R. et al., Nat Genet, 18:106-08, 1998; Polmeropoulos, M H, et al., Science, 276:2045-47, 1997; Zarranz, J J, et al., Ann Neurol, 55: 164-73, 2004). α-syn gene multiplication, causing an increase in the amount of normal α-syn present, is sufficient to trigger PC (Singleton, A B, et al., Science, 302:841, 2003). In addition α-syn aggregates are observed in sporadic PD (Spillantini, M G, et al., Nature, 388:839-40, 1997) and insoluble α-syn is increased in sporadic PD and the related condition Dementia with Lewy Bodies (DLB) (Cantuti-Castelverti, I, et al., J Neuropathol Exp Neurol, 64:1058-66, 2005). Furthermore, transgenic mice expressing mutant or wild-type α-syn show motor deficits, alterations in dopaminergic terminals and α-syn positive inclusions (Maries, E, et al., Nat Rev Neurosci, 4:727-38, 2003). Rats and primates virally injected with mutant or wild-type α-syn into the substantia nigra show nigral dopaminergic cell loss (Maries, E, et al., Nat Rev Neurosci, 4:727-38, 2003).

The art is currently in need of novel methods for the treatment and prevention of neurodegeneration and diseases associated with neurodegeneration. Although 14-3-3 proteins are implicated in neurodegeneration in a variety of models, the mechanisms by which 14-3-3 proteins contribute to such neurodegeneration are poorly understood. As a result, therapies for treatment and prevention of neurodegeneration are currently lacking. The present disclosure provides novel methods for the prevention and treatment of neurodegeneration and disease states characterized, at least in part, by neurodegeneration.

BRIEF DESCRIPTION OF THE FIGURES

FIGS. 1A-G show the amino acid sequence of 14-3-3 polypeptide isoforms β (FIG. 1A), γ FIG. 1B), ε (FIG. 1C), ζ (FIG. 1D), η (FIG. 1E), θ (FIG. 1F) and FIG. 1G shows a sequence comparison of the human 14-3-3 isoforms. Residues conserved over 6 isoforms are shaded.

FIG. 5A shows a Western blot of stably transfected 14-3-3θ cells. 14-3-3θ was subcloned into the pcDNA3.1/V5-His vector, and SK-N-BE (2)-M17 cells were transfected with V5/his-tagged 14-3-3θ construct. Cells stably transfected with 14-3-3θ were selected for in the presence of G418. 13 different clones were analyzed for their expression of 14-3-3θ. Protein lysates of these clones were blotted with a monoclonal antibody against V5 to detect exogenous 14-3-3θ (top blot) or with a monoclonal antibody against 14-3-3θ to detect total 14-3-3θ levels (exogenous or endogenous; bottom blot). Two clones (clones 4 and 5) with high levels of 14-3-3θ overexpression were used for further experiments.

FIG. 6D shows M17 cells transiently transfected with V5/his-tagged 14-3-3θ construct plasmid into naïve M17 cells. Control cells were transfected with GFP. 24 hours after transfection, cells were treated with rotenone at 0, 0.2, or 1 μM for 24 hours. Afterwards, cells were fixed and immunostained with an antibody against V5 or GFP, followed by nuclear staining with Hoechst 33342. Nuclei of transfected cells were scored as normal or showing apoptotic changes. Rater was blind to experimental condition. n=8 for each experimental condition. *p<0.05, ***p<0.001 (Bonferroni's multiple comparison test).

FIG. 7A shows four different shRNAs targeting 14-3-3θ showed considerable knockdown of 14-3-3θ protein expression. Naïve M17 cells were infected with a pLKO.1 lentiviral construct containing one of four different 14-3-3θ-specific shRNA sequences. Control cells were infected with an empty pLKO.1 lentiviral construct (with no shRNA sequence). Infected cells were selected for in the presence of puromycin. Protein lysates from these infected cells were immunoblotted with a monoclonal antibody against 14-3-3θ (top band). Immunoblotting against tubulin (bottom band) shows comparable protein loading.

DETAILED DESCRIPTION

Definitions

Figure 1G:
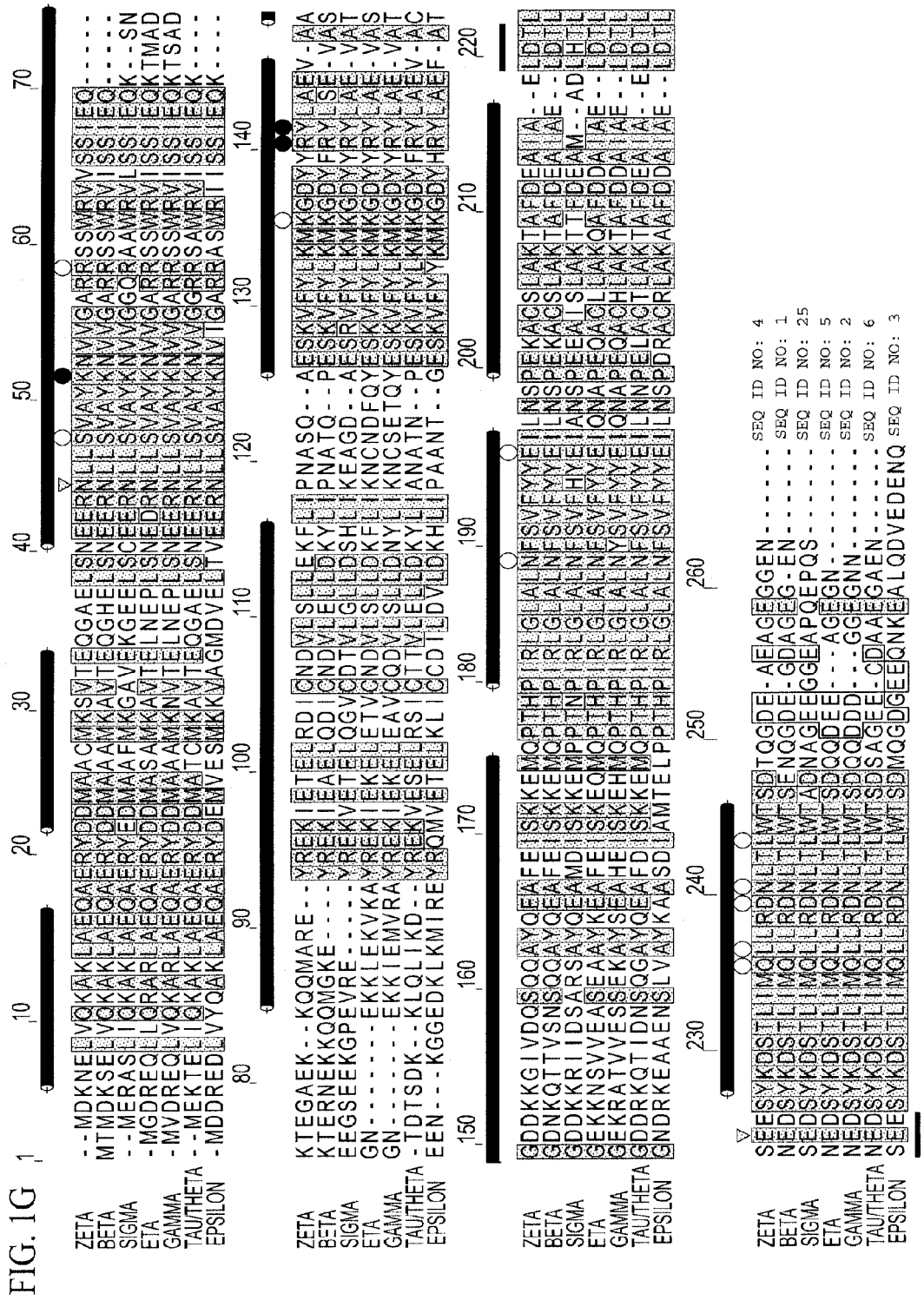

The term "14-3-3 polypeptide" as used herein refers to a member of the 14-3-3 protein family, including, but not limited to, the various isoforms (β, γ, ε, ζ, η, θ and σ). When specified, the term can refer to a specific isoform or group of isoforms. In one embodiment, the term refers to at least one of the γ, ε or β isoforms. The amino acid sequence of the β, γ, ε, ζ, η, θ isoforms are provided in FIG. 1A-F. FIG. 1G provides a sequence alignment of human 14-3-3 isoforms. Residues conserved across a minimum of six isoforms are shaded in gray. Any nucleic acid sequence encoding such amino acid sequences may be used to generate such isoforms.

The term "14-3-3 polypeptide derivative" as used herein refers to a 14-3-3 polypeptide that includes a one or more insertions, deletions or substitutions. The 14-3-3 polypeptide derivative may have an activity that is comparable to or increased (in one embodiment, 50% or more) as compared to the wild-type 14-3-3 polypeptide activity and as such may be used to increase a 14-3-3 polypeptide activity; alternatively, the 14-3-3 polypeptide derivative may have an activity that is decreased (in one embodiment, less than 50%) as compared to the wild-type 14-3-3 polypeptide activity and as such may be used to decrease a 14-3-3 polypeptide activity. A 14-3-3 polypeptide derivative includes those sequences that are at least 50, 75, 90, 95 or 99% identical to the sequences shown in FIG. 1A-G.

The term "a 14-3-3 polypeptide activity" as used herein refers broadly to an activity mediated by a 14-3-3 polypeptide with respect to a particular polypeptide bound by a 14-3-3 polypeptide (referred to as binding target). As discussed herein, 14-3-3 polypeptides bind a number of binding targets with a wide range of activities. In general, a 14-3-3 protein regulates the activity of binding targets in three ways: (i) by direct regulation of the catalytic activity of the bound binding target (binding to a 14-3-3 protein can change the conformation of the binding target without the 14-3-3 polypeptide undergoing significant conformational change itself); (ii) by regulating interactions between the binding target and other molecules in the cell by sequestration or modification; (iii) or by controlling the sub-cellular localization of the binding target. Each of these activities can either increase or decrease the activity of the binding target, depending on the nature of the binding target and the cellular environment. In the specification, the 14-3-3 polypeptide activity refers to a function of the wild-type 14-3-3 polypeptide. In one embodiment, a 14-3-3 polypeptide activity is determined with regard to the BAD binding target. An increase in 14-3-3 polypeptide activity refers to a manipulation that results in more of the activity; a decrease in 14-3-3 polypeptide activity refers to a manipulation that results in less of the activity. Methods of increasing or decreasing a 14-3-3 polypeptide activity are disclosed herein. In one embodiment, an increase in 14-3-3 polypeptide activity is accomplished by increasing the levels of 14-3-3 polypeptide. An increase in 14-3-3 polypeptide levels can be accomplished by increasing the transcription of genes encoding a 14-3-3 polypeptide, by altering the localization of the 14-3-3 polypeptide, increasing the stability of a 14-3-3 polypeptide or decreasing the rate of degradation of a 14-3-3 polypeptide. In an alternate embodiment, a decrease in 14-3-3 polypeptide activity is accomplished by decreasing the levels of 14-3-3 polypeptide. A decrease in 14-3-3 polypeptide levels can be accomplished by decreasing the transcription of genes encoding a 14-3-3 polypeptide, by altering the localization of the 14-3-3 polypeptide, decreasing the stability of a 14-3-3 polypeptide or increasing the rate of degradation of a 14-3-3 polypeptide The terms "prevention", "prevent", "preventing", "suppression", "suppress" and "suppressing" as used herein refer to a course of action initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Methods of Treatment and Prevention

The present disclosure describes the modulation of 14-3-3 polypeptide expression or of a 14-3-3 polypeptide activity for use in the treatment of human disease.

In one embodiment, 14-3-3 polypeptide expression is increased and/or a 14-3-3 polypeptide activity is increased. In a specific embodiment, 14-3-3$\zeta$, $\gamma$, $\epsilon$ and/or $\theta$ expression is increased or a 14-3-3 polypeptide activity mediated by at least one of the $\zeta$, $\gamma$, $\epsilon$ and $\theta$ isoforms is increased; in a further specific embodiment, 14-3-3$\theta$ expression is increased or a 14-3-3 polypeptide activity mediated by the $\theta$ isoform is increased. By increasing 14-3-3 polypeptide expression/activity, the present disclosure provides for methods of treatment and/or prevention of disease states that are characterized, at least in part, by decreased 14-3-3 polypeptide expression/activity. In a specific embodiment, the disease state is characterized by a decrease in 14-3-3$\zeta$, $\gamma$, $\epsilon$ and/or $\theta$ expression or a decrease in 14-3-3 polypeptide activity mediated by at least one of the $\zeta$, $\gamma$, $\epsilon$ and $\theta$ isoforms. In a further specific embodiment, the disease state is characterized by a decrease in 14-3-3$\theta$ expression or by a decrease in 14-3-3 polypeptide activity mediated by the $\theta$ isoform. In one embodiment, the disease state is neurodegeneration and/or diseases characterized, at least in part, by neurodegeneration. In an alternate embodiment, the disease state is PD. By increasing a 14-3-3 polypeptide expression/activity, the function of the 14-3-3 polypeptide is restored, at least in part, thereby treating or preventing disease states that are characterized, at least in part, by a decreased 14-3-3 polypeptide activity.

Exemplary diseases characterized, at least in part, by neurodegeneration include, but are not limited to, Alper's disease, Alzheimer's disease, amyotrophic lateral sclerosis, ataxia telangiectasia, Batten disease, bovine spongiform encephalopathy (BSE), Canavan disease, Cockayne syndrome, corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), multiple sclerosis, multiple system atrophy, narcolepsy, neuroborreliosis, Parkinson's disease (PD), Pelizaeus-Merzbacher disease, Pick's disease, primary lateral sclerosis, pr, Refsum's disease, Sandhoff disease and Schilder's disease. In a specific embodiment, the disease is PD.

Activating a 14-3-3 polypeptide activity can be accomplished in a number of ways, including but not limited to, increasing the absolute levels of the products of 14-3-3 gene expression, increasing the expression level or rate of 14-3-3 gene expression, increasing the stability of the polypeptide products of 14-3-3 gene expression, increasing the levels and/or activity of a 14-3-3 polypeptide, introducing a 14-3-3 polypeptide derivative, increasing or decreasing the activity or expression of a binding target of a 14-3-3 polypeptide or a combination of any of the foregoing. Such activation may be achieved by direct or indirect methods. For example, direct methods may include, but are not limited to, providing increased levels of a 14-3-3 polypeptide, increasing the stability or activity of a 14-3-3 polypeptide or introducing a 14-3-3 polypeptide derivative. Indirect methods may include, but are not limited to, the increasing the activity or expression of polypeptides that activate a 14-3-3 proteins activity or decreasing the activity or expression of polypeptides that inhibit a 14-3-3 protein activity, such as but not limited to α-syn. Any of the above may be accomplished through the administration of a pharmaceutical composition comprising at least one active ingredient or biologic or via the artificial induction of nucleic acid molecules encoding a 14-3-3 polypeptide or a 14-3-3 polypeptide derivative.

In one embodiment, a nucleic acid molecule may be used to allow for or increase the expression of a 14-3-3 polypeptide or a 14-3-3 polypeptide derivative. The proper selection of 14-3-3 polypeptide derivatives is discussed herein. Such nucleic acid molecules may be use in gene therapy methods to introduce or increase the expression of a 14-3-3 polypeptide or a 14-3-3 polypeptide derivative. The polypeptide product may then be expressed and the treatment and/or prevention accomplished. Many methods exist for the introduction of nucleic acid molecules into a subject. For example, the nucleic acid molecule may be introduced into a vector and introduced into the patient such that the nucleic acid is expressed and the therapeutic potential realized. Exemplary methods of introduction include, but are not limited to, viral vectors (including retroviruses) and liposomes. Vectors may be introduced into a patient either in vivo or ex vivo. In the case of an in vivo treatment, the vector may be simply injected into the patient, for example parenterally, and allowed to find suitable target cells for gene expression or into a specific tissue, such as neural tissue, by intrathecal or intracranial injection. In the case of ex vivo treatment, cells are grown in vitro and transduced or transfected with the virus, embedded in a carrier such as a collagen matrix, which is then implanted in the patient, for example as a sub-cutaneous implant.

The expression of 14-3-3s is regulated at both the gene and protein levels. 14-3-3σ is down-regulated in multiple cancers, including breast, lung, and colon carcinoma, and the expression level of 14-3-3σ correlates with the stage of disease. 14-3-3ζ, γ, ε and θ 14-3-3ζ, γ, ε and θ have also been shown to be down-regulated in the present disclosure. Such down-regulation may occur via epigenetic mechanisms. Two possible mechanisms include promotion of DNA methylation or inhibition of histone acetylation of 14-3-3 genes. Hypermethylation of CpG islands in the 5' region of 14-3-3σ has been shown to be the mechanism by which 14-3-3σ is silenced in several cancers. 5'-aza-2'-deoxycytidine, mitoxanthrone, and the histone deacetylase inhibitor AN-9 (pivaloyloxymethyl butyrate) can demethylate the 14-3-3σ gene and induce re-expression of the silenced gene in breast cancer cell (Parker, et al, Cancer Biol Ther 2, 259-63 2003; Ferguson et al., Proc Natl Acad Sci USA 97, 6049-54, 2000). Several of the 14-3-3 genes have CpG-rich regions which may serve as targets for DNA methylation. Interestingly, 14-3-3θ is most similar to 14-3-3σ by homology. Therefore, treatment with agents that decrease methylation, such as, but not limited to, 5'-aza-2'-deoxycytidine, mitoxanthrone, and AN-9 (pivaloyloxymethyl butyrate), may increase 14-3-3 polypeptide expression and increase 14-3-3 polypeptide activity.

Recent evidence suggests that α-syn could affect transcription by inhibition of histone acetylation. First, α-syn can be found in the nucleus where it could have an effect on transcription. Second, α-syn has been shown to associate with histones in in vitro studies. Direct evidence of α-syn's ability to inhibit histone acetylation was shown in studies pursued by Kontopoulos et al (Hum Mol Genet. 15, 3012-23, 2006) in both cell culture and transgenic *Drosophila*. Their studies showed that α-syn decreased the levels of acetylated histone H3 in cell culture and prevented acetylation in histone acetyltransferase assays. This effect on histone acetylation appears to be critical to α-syn-induced toxicity as treatment with histone deacetylase inhibitors rescues cells against α-syn toxicity in both cell culture and *Drosophila* models [33]. Indeed, the inhibition of 14-3-3 transcription by α-syn could lead to a negative feedback loop, meaning a self-perpetuating decrease, since 14-3-3s themselves inhibit the activity of histone deacetylases (Grozinger et al., Proc Natl Acad Sci USA 97, 7835-40 2000). Therefore, treatment with histone deacetylase inhibitor, such as, but not limited to, AN-9 (pivaloyloxymethyl butyrate), may increase 14-3-3 polypeptide expression and increase 14-3-3 polypeptide activity.

14-3-3 expression can also be regulated at the protein level. In breast cancer, Efp, a E3 ubiquitin ligase, targets 14-3-3σ for ubiquitin-mediated proteolysis (Urano et al., Nature 417, 871-5, 2002). 14-3-3s have also been demonstrated to be substrates for activated caspases (Won et al., 3 Biol Chem 278, 19347-51, 2003). Phosphorylation of 14-3-3s prevents their dimerization and regulates the ability to bind targets. Therefore, treatment with ubiquitin ligase and caspase inhibitors may increase 14-3-3 polypeptide expression and increase 14-3-3 polypeptide activity.

Peroxisome proliferator-activated receptors (PPARs) are ligand inducible transcription factors that control a wide range of functions. Three isotypes have been identified in vertebrates: PPARα; PPARγ and PPARδ. PPARs have been implicated as being involved in similar processes as 14-3-3 proteins, suggesting that PPARs may be regulators of 14-3-3 expression and/or activity. Recent evidence indicates that PPARδ increased 14-3-3ε expression and that this regulation was dependent on CCATT/enhancer binding protein (C/EBP) sites and PPARδ regulated C/EBPβ protein expression (Brunelli, et al., Circulation Research, 100:e59-e71, 2007, which reference is incorporated herein in its entirety). Furthermore, 14-3-3ζ, γ, ε and θ have functional C/EBP sites that contribute to regulation of expression. Therefore, 14-3-3 expression may be regulated by PPAR agonists.

In principle, any compound known or discovered to have PPAR gamma or delta agonist activity may be used in the invention, but compounds suitable for oral administration are preferred; dual activity agonists may also be use (including PPAR alpha/gamma agonists). Suitable PPAR agonists include, but are not limited to, MCC-555, GW1929, KRP-297 (MK-0767), muraglitazar (BMS-298585), farglitazar, ragaglitazar, tesaglitazar (AZ-242), JT-501, GW-2570, GI-262579, CLX-0940, GW-1536, GW-1929, GW-2433), L-796449, LR-90, SB-219994, LY-578, LY-4655608, LSN-862, LY-510929, LY-929, ETYA, AZ242, oleyethanolamide, tetradecylthioacetic acid, WY-14643, LY171883, 15d-PGJ2, tesaglitazar, thiazolidinediones, thiazolidinedione, and include: rosiglitazone, pioglitazone, troglitazone, rivoglitazone and ciglitazone. Other suitable PPAR agonists are described in WO/2005/115369 (annexes A, B and C), WO/2005/053670, WO 97/28115, WO 00/78312, WO 00/78313, WO 00/196321, WO 00/181327, WO 00/134148, WO 02/064094, WO 02/060434, WO 02/26729, WO 01/60807, EP1194147, EP1194146, WO 03/066581 WO 03/075911, US Patent Publication 20070179191 Collins et al., *J. Med. Chem.*, 41 (25), 5037-5054, 1998, Bioorg. Med. Chem. Lett., 2003, 13, 3541-4, Bioorg Med. Chem. Lett., 2003, 13, 2795 and Rational drug design and PPAR Agonists, ISSN 1534-4827 (Print) 1539-0829 volume 5, Number 5/September, 2005 (Online). The foregoing references are hereby incorporated by reference for their teaching relating to PPAR agonists.

Therefore, the present disclosure provides for methods to treat and/or prevent disease states characterized, at least in part, by a decreased 14-3-3 polypeptide activity. In a specific embodiment, the disease state is characterized by a decrease in 14-3-3 polypeptide activity mediated by at least one of the η, γ, ε and θ isoforms. In a further specific embodiment, the disease state is characterized by a decrease in 14-3-3 polypeptide activity mediated by the θ isoform.

Furthermore, the present disclosure provides for methods to treat and/or prevent neurodegeneration or diseases characterized, at least in part, by neurodegeneration in a subject in need of such treatment and/or prevention. The present disclosure also provides for methods to treat and/or prevent diseases which depend on a neurodegenerative process in their etiology in a subject in need of such treatment and/or prevention.

Still further, the present disclosure provides for methods to treat and/or prevent PD in a subject in need of such treatment and/or prevention In one embodiment, the methods of treatment and/or prevention comprise the steps of initiating in a subject a therapeutic regimen that increases a 14-3-3 polypeptide activity. In a specific embodiment the therapeutic regimen increases a 14-3-3-polypeptide activity mediated by the ζ, γ, ε and θ isoforms. In a further specific embodiment, the therapeutic regimen increases a 14-3-3-polypeptide activity mediated by the θ isoform.

Methods for increasing a 14-3-3 polypeptide activity are discussed herein. In a specific embodiment, a 14-3-3 polypeptide activity is increased by increasing the levels of a 14-3-3 polypeptide or introducing a 14-3-3 polypeptide or 14-3-3 polypeptide derivative in the subject. Such increased expression may be accomplished by administering a compound or pharmaceutical composition containing at least one active ingredient capable of increasing the expression of a 14-3-3 polypeptide. In a specific embodiment, the expression of at least one of the 14-3-3 ζ, γ, ε and θ isoforms is increased. In a further embodiment, the expression of the 14-3-3θ isoform is increased. In an alternate embodiment, such increased expression may be accomplished by introducing a nucleic acid molecule encoding a 14-3-3 polypeptide or a 14-3-3 polypeptide derivative into a tissue (such as a neural tissue, including but not limited to the substantia nigra) of said subject. In a specific embodiment, such nucleic acid encodes at least one of a ζ, γ, ε and θ isoform. In a further specific embodiment, such nucleic acid encodes a θ isoform. Such an increase in a 14-3-3 polypeptide activity would thereby treat and/or prevent a disease state characterized, at least in part, by a decreased 14-3-3 polypeptide activity, such as neurodegeneration, in a subject.

As discussed above, a 14-3-3 polypeptide activity is broadly defined to include any activity mediated by a wild-type 14-3-3 polypeptide. Without limiting the generality of the foregoing, in one embodiment, a 14-3-3 polypeptide activity is the maintenance of certain activities of its binding target in a down-regulated state. In some neurodegenerative diseases, the overexpression of certain polypeptides (such as but not limited to α-syn) disrupts the ability of a 14-3-3 polypeptide to perform this function by binding to a 14-3-3 polypeptide and displacing the binding target or preventing the binding target from interacting with a 14-3-3 polypeptide. In addition, in some neurodegenerative diseases, the expression of certain 14-3-3 polypeptides is down-regulated. As a result of the foregoing, 14-3-3 polypeptide activity is decreased. In these cases, the activity of the binding target is not maintained in a down-regulated state and the binding target exerts a deleterious effect on the subject which results in neurodegeneration.

Methods of Diagnosis

The present disclosure also provides methods of diagnosis for determining the status of a subject with respect to a 14-3-3 polypeptide or a 14-3-3 polypeptide activity. In one embodiment, such methods determine in the subject the level of a 14-3-3 polypeptide, either in total or with respect to a particular isoform or a 14-3-3 polypeptide activity. In one embodiment, the isoform is at least one of the 14-3-3 ζ, γ, ε and β isoforms; in an alternate embodiment the isoform is θ. In another embodiment of such methods, the level of a polypeptide bound to a 14-3-3 polypeptide may be determined, such as but not limited to, α-syn.

The present disclosure provides for the first time the identification of specific 14-3-3 isoforms involved in degenerative neurological process, such as, but not limited to PD. The isoforms identified include at least one of 14-3-3 ζ, γ, ε and θ. Therefore, the present disclosure provides methods for diagnosing a subject as suffering from or at risk for a disease characterized, at least in part, by neurodegeneration. The present disclosure farther provides methods for diagnosing a subject as suffering from or at risk for PD. The disclosed methods comprise obtaining a sample from a subject and determining the levels of expression of at least one of the 14-3-3 ζ, γ, ε and/or θ isoforms or determining a 14-3-3 polypeptide activity mediated by at least one of the 14-3-3 ζ, γ, ε and/or θ isoforms. The level of expression of the desired 14-3-3 isoform(s) may be compared to a control sample taken from a subject that is determined not to be suffering from or at risk for PD or a disease characterized at least in part by neurodegeneration. According to one embodiment of such a method, the detecting can be performed, for example, by obtaining a cell, tissue, bodily fluid or a biological sample from the subject and contacting the foregoing with one or more reagents capable of detecting 14-3-3 expression levels or 14-3-3 polypeptide activity; the methods described herein may be used. In one embodiment, the determination is made in a neural tissue of the subject, such as, but not limited to, the substantia nigra, cortex of Lewy bodies. In such methods, the presence of decreased level of 14-3-3 ζ, γ, ε and/or θ polypeptide or a decreased 14-3-3 polypeptide activity mediated by 14-3-3 ζ, γ, ε and θ (as compared to controls) is indicative that the subject is suffering from or at risk for PD or a disease characterized, at least in part, by neurodegeneration.

The level of expression may be determined at the protein level or at the level of gene expression. Assay techniques that can be used to determine levels of expression or activity in a sample are known. Such assay methods include, but are not limited to, radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radioimmunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. Nos. 4,845,026 and 5,006,459.

In an ELISA assay, an antibody is prepared, if not readily available from a commercial source, specific to an antigen, such as, for example, 14-3-3 ζ, γ, ε and/or θ. In addition, a reporter antibody generally is prepared which binds specifically to the antigen. The reporter antibody is attached to a detectable reagent such as a radioactive, fluorescent or enzymatic reagent, for example horseradish peroxidase enzyme or alkaline phosphatase. To carry out the ELISA, antibody specific to antigen is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time the antigen binds to the specific antibody attached to the polystyrene dish. Unbound sample is washed out with buffer. A reporter antibody specifically directed to the antigen and linked to a detectable reagent such as horseradish peroxidase is placed in the dish resulting in binding of the reporter antibody to any antibody bound to the antigen. Unattached reporter antibody is then washed out. Reagents for peroxidase activity, including a calorimetric substrate are then added to the dish. Immobilized peroxidase, linked to antibodies, produces a colored reaction product. The amount of color developed in a given time period is proportional to the amount of antigen present in the sample. Quantitative results typically are obtained by reference to a standard curve. Suitable antibodies for use in these methods are disclosed herein.

Optionally, a genetic sample from the biological sample can be obtained. The genetic sample comprises a nucleic acid, preferably RNA and/or DNA. For example, in determining the expression of genes mRNA can be obtained from the biological sample, and the mRNA may be reverse transcribed into cDNA for further analysis. Alternatively, the mRNA itself is used in determining the expression of genes.

A genetic sample may be obtained from the biological sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984)). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423:17 28, 1999).

Once a genetic sample has been obtained, it can be analyzed. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, and the like. In determining the expression level of a gene or genes in a genetic sample, the level of expression may be normalized by comparison to the expression of another gene such as a well known, well characterized gene or a housekeeping gene. For example, reverse-transcriptase PCR (RT-PCR) can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Suitable primers and probes for detecting the relevant isoforms are disclosed herein.

Hybridization to clones or oligonucleotides arrayed on a solid support (i.e., gridding) can be used to both detect the expression of and quantitate the level of expression of that gene. In this approach, a cDNA encoding an antigen is fixed to a substrate. The substrate may be of any suitable type including but not limited to glass, nitrocellulose, nylon or plastic. At least a portion of the DNA encoding the antigen is attached to the substrate and then incubated with the analyte, which may be RNA or a complementary DNA (cDNA) copy of the RNA, isolated from the sample of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Methods of Screening

The present disclosure also relates to a method for identifying a compound effective for treating or preventing PD or a disease characterized, at least in part, by decreased 14-3-3 expression, such as, but not limited to, neurodegeneration. In one embodiment, such a screening assay can be performed, for example, by determining in an appropriate model system (such as, but not limited to, those systems described herein) the level of a 14-3-3 $\zeta$, $\gamma$, $\epsilon$ and/or $\theta$ polypeptide, the level of mRNAs encoding 14-3-3 $\zeta$, $\gamma$, $\epsilon$ and/or $\theta$ polypeptide, a 14-3-3 polypeptide activity mediated by 14-3-3 $\zeta$, $\gamma$, $\epsilon$ and/or $\theta$ polypeptide, the level of a polypeptide bound to a 14-3-3 polypeptide, such as but not limited to, $\alpha$-syn, or the amount of aggregation, and detecting a difference in the level or activity of the foregoing in the presence of as compared to the absence of the compound. In specific embodiment, the screening assay may be in vitro, in vivo or ex vivo and may be cell culture based (either with whole cells or lysates) or may be based on an animal model. A screening assay of the disclosure is particularly amenable to a high throughput format, thereby providing a means to screen, for example, a combinatorial library of small organic molecules, peptides, nucleic acid molecules, and the like. In a particular embodiment, the disease is PD, although any disease that is characterized at least in part by neurodegeneration may be diagnosed or screened.

Such a screening methods comprise the steps of providing a cell/system that expresses 14-3-3 $\zeta$, $\gamma$, $\epsilon$ and/or $\theta$, contacting the cell/system with a candidate agent to be tested and determining whether the candidate agent enhances the expression or activation of 14-3-3 $\zeta$, $\gamma$, $\epsilon$ and/or $\theta$. Another method of screening for agents that increase the activity of 14-3-3 $\zeta$, $\gamma$, $\epsilon$ and/or $\theta$ comprises the steps of providing a sample comprising 14-3-3 $\zeta$, $\gamma$, $\epsilon$ and/or $\theta$, contacting the sample with a candidate agent to be tested and determining whether the candidate agent increases the activation of 14-3-3 $\zeta$, $\gamma$, $\epsilon$ and/or $\theta$. The provided cells that express 14-3-3 $\zeta$, $\gamma$, $\epsilon$ and/or $\theta$ can be made by infecting the cell with a virus comprising 14-3-3 $\zeta$, $\gamma$, $\epsilon$ and/or $\theta$ wherein the 14-3-3 $\zeta$, $\gamma$, $\epsilon$ and/or $\theta$ is expressed in the cell following infection. The cell can also be a prokaryotic or an eukaryotic cell that has been transfected with a nucleotide sequence encoding 14-3-3 $\zeta$, $\gamma$, $\epsilon$ and/or $\theta$ or a variant or a fragment thereof operably linked to a promoter. Using DNA recombination techniques well known by the one skill in the art, protein encoding DNA sequences can be inserted into an expression vector, downstream from a promoter sequence. Alternatively, the cell expressing 14-3-3 $\zeta$, $\gamma$, $\epsilon$ and/or $\theta$ may optionally express naturally express 14-3-3 $\zeta$, $\gamma$, $\epsilon$ and/or $\theta$.

Such methods allow one skilled in the art to select candidate agents that increase 14-3-3 $\zeta$, $\gamma$, $\epsilon$ and/or $\theta$ expression or activity. Such agents may be useful as active ingredients included in pharmaceutical compositions. Methods for determining whether the candidate agent increases expression or activation of 14-3-3 $\zeta$, $\gamma$, $\epsilon$ and/or $\theta$ are known. The assay can be, for example, one of the provided methods described in the present application.

Kits

The present disclosure also provides kits for carrying out any method of the present disclosure, which can contain any of the compounds and/or compositions disclosed herein or otherwise useful for practicing a method of the disclosure. For example, a kit for carrying out methods for diagnosing a subject as suffering from or at risk for PD ma contain a probe/primer/antibody specific to a relevant 14-3-3 isoform as disclosed above, appropriate reagents and buffers for determining 14-3-3 expression and instructions for carrying out the methods.

Creation and Selection of 14-3-3 Polypeptide Derivatives

As discussed above, the 14-3-3 proteins are a large family of approximately 30 kDa acidic proteins which exist primarily as homo- and heterodimers within all eukaryotic cells. There is a high degree of sequence identity and conservation between all the 14-3-3 isotypes, particularly in the regions which form the dimer interface or line the central ligand binding channel of the dimeric molecule. Each 14-3-3 protein sequence can be roughly divided into three sections: a divergent amino terminus, the conserved core region and a divergent carboxyl terminus. The conserved middle core region of the 14-3-3s encodes an amphipathic groove that forms the main functional domain, a cradle for interacting with client proteins. The monomer consists of nine helices organized in an antiparallel manner, forming an L-shaped structure. The interior of the L-structure is composed of four helices: H3 and H5, which contain many charged and polar amino acids, and H7 and H9, which contain hydrophobic amino acids. These four helices form the concave amphipathic groove that interacts with the binding targets.

14-3-3 proteins mainly bind proteins containing phosphothreonine or phosphoserine motifs, although 14-3-3 polypeptides have been reported to bind target that are not so phosphorylated. Extensive investigation of the 14-3-3 binding site of the mammalian serine/threonine kinase Raf-1 has produced a consensus sequence for 14-3-3-binding, RSxpSxP (in the single-letter amino-acid code, where x denotes any amino acid and p indicates phospho-serine). 14-3-3 proteins appear to effect intracellular signaling in one of three ways—by direct regulation of the catalytic activity of the binding target, by regulating interactions between the bound binding target and other molecules in the cell by sequestration or modification or by controlling the subcellular localization of the bound binding target. Proteins appear to initially bind to a single dominant site and then subsequently to many, much weaker secondary interaction sites. The 14-3-3 dimer is capable of changing the conformation of its bound ligand whilst itself undergoing minimal structural alteration.

The present disclosure contemplates the use of 14-3-3 polypeptide derivatives in the methods of treatment and prevention disclosed herein. As defined herein refers to a 14-3-3 polypeptide that includes a one or more insertions, deletions or substitutions. The 14-3-3 polypeptide derivative may have an activity that is comparable to or increased (in one embodiment, 50% or more) as compared to the wild-type 14-3-3 polypeptide activity and as such may be used to increase a 14-3-3 polypeptide activity; alternatively, the 14-3-3 polypeptide derivative may have an activity that is decreased (in one embodiment, less than 50%) as compared to the wild-type 14-3-3 polypeptide activity and as such may be used to decrease a 14-3-3 polypeptide activity.

The deletions, additions and substitutions can be selected, as would be known to one of ordinary skill in the art, to generate a desired 14-3-3 polypeptide derivative. For example, it is not expected that deletions, additions and substitutions in the divergent amino and carboxy terminus of a 14-3-3 polypeptide would alter a 14-3-3 polypeptide activity. Likewise conservative substitutions or substitutions of amino acids with similar properties is expected to be tolerated in the conserved middle region, particularly in helices H3, H5, H7 and H9, and a 14-3-3 polypeptide activity may be conserved. Of course non-conservative substitutions in these regions would be expected to decrease or eliminate a 14-3-3 polypeptide activity. In addition, specific deletions, insertions and substitutions may impact, positively or negatively, a certain 14-3-3 polypeptide activity but not impact a different 14-3-3 polypeptide activity.

Conservative modifications to the amino acid sequence of any of SEQ ID NOS:1-6, including combinations thereof (and the corresponding modifications to the encoding nucleotides) will produce 14-3-3 polypeptide derivatives having functional and chemical characteristics similar to those of naturally occurring 14-3-3 polypeptides. In contrast, substantial modifications in the functional and/or chemical characteristics of 14-3-3 polypeptides may be accomplished by selecting substitutions in the amino acid sequence of any of SEQ ID NOS:1-6, including combinations thereof, that differ significantly in their effect on maintaining (a) the structure of the molecular backbone in the area of the substitution, for example, one of the helices contained in the core region, (b) the charge or hydrophobicity of the molecule at the binding site for a binding target, such as for example, one or more of helices H3, H5, H7 and H9, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine.

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

For example, non-conservative substitutions may involve the exchange of a member of one of these classes for a member from another class. Such substituted residues may be introduced into regions of the 14-3-3 polypeptide derivatives that are homologous with non-human 14-3-3 polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (Kyte et al., J. Mol. Biol., 157:105-131, 1982). It is known that certain amino acids may be substituted for other amino acids having a similar hydropathic index or score and still retain a similar biological activity.

In making changes based upon the hydropathic index, the substitution of amino acids whose hydropathic indices are within +/−2 may be used; in an alternate embodiment, the hydropathic indices are with +/−1; in yet another alternate embodiment, the hydropathic indices are within +/−0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein.

The following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +/−2 may be used; in an alternate embodiment, the hydrophilicity values are with +/−1; in yet another alternate embodiment, the hydrophilicity values are within +/−0.5.

Desired amino acid substitutions (whether conservative or non-conservative) can be determined by those skilled in the art at the time such substitutions are desired. For example, amino acid substitutions can be used to identify important residues of the 14-3-3 polypeptide, or to increase or decrease the affinity of the 14-3-3 polypeptide with a particular binding target in order to increase or decrease a 14-3-3 polypeptide activity.

Exemplary amino acid substitutions are set forth in the table 1 below

TABLE 1

| Original Amino Acid | Exemplary substitution | Preferred substitution |
|---|---|---|
| Ala | Val, Leu, Ile | Val |
| Arg | Lys, Gln, Asn | Lys |
| Asn | Glu | Glu |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4-diaminobutyric acid, Gln, Asn | Arg |
| Met | Leu, Phe, Ile | Leu |
| Phe | Len, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NOS:1-6, including combinations thereof, using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a 14-3-3 polypeptide to such similar polypeptides. With such a comparison, one can identify residues and portions of the molecules that are conserved among similar polypeptides. It will be appreciated that changes in areas of a 14-3-3 polypeptide that are not conserved relative to such similar polypeptides would be less likely to adversely affect the biological activity and/or structure of the 14-3-3 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a 14-3-3 polypeptide that correspond to amino acid residues that are important for activity or structure in similar polypeptides. One skilled in the art may opt for chemically similar amino acid substitutions for such predicted important amino acid residues of 14-3-3 polypeptide.

One skilled in the art can also analyze the three-dimensional structure and amino acid sequence in relation to that structure in similar polypeptides. In view of that information, one skilled in the art may predict the alignment of amino acid residues of a 14-3-3 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test 14-3-3 polypeptide derivatives containing a single amino acid substitution at each desired amino acid residue. The derivatives can then be screened using activity assays know to those skilled in the art and as disclosed herein. Such derivatives could be used to gather information about suitable substitution. For example, if one discovered that a change to a particular amino acid residue resulted in destroyed, undesirably reduced, or unsuitable activity, derivatives with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure from analyses of amino acid sequences (see Chou et al., Biochemistry, 13(2):222-245, 1974; Chou et al., Biochemistry, 113(2):211-222, 1974; Chou et al., Adv. Enzymol. Relat. Areas Mol. Biol., 47:45-148, 1978; Chou et al., Ann. Rev. Biochem., 47:251-276, 1979; and Chou et al., Biophys. J., 26:367-384, 1979). Moreover, computer programs are currently available to assist with predicting secondary structure of polypeptides. Examples include those programs based upon the Jameson-Wolf analysis (Jameson et al., Comput. Appl. Biosci., 4(1):181-186, 1998; and Wolf et al., Comput. Appl. Biosci., 4(1):187-191; 1988), the program PepPlot® (Brutlag et al., CABS, 6:237-245, 1990; and Weinberger et al., Science, 228:740-742, 1985), and other new programs for protein tertiary structure prediction (Fetrow. et al., Biotechnology, 11:479-483, 1993).

Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure (see Holm et al., Nucl. Acid. Res., 27(1):244-247, 1999).

Additional methods of predicting secondary structure include "threading" (Jones, D., Curr. Opin. Struct. Biol., 7(3): 377-87, 1997; Suppl et al., Structure, 4(1):15-9, 1996), "profile analysis" (Bowie et al., Science, 253:164-170, 1991; Gribskov et al., Meth. Enzym., 183:146-159, 1990; and Gribskov et al., Proc. Nat. Acad. Sci., 84(13): 4355

Compositions

Useful compositions of the present disclosure may comprise one or more compounds useful in the treatment and prevention methods of the present disclosure, such as, but not limited to, those compounds identified in the present disclosure or identified by a screening method of the present disclosure. In one embodiment, such compounds decrease a 14-3-3 polypeptide activity. In an alternate embodiment, such compounds increase a 14-3-3 polypeptide activity. In one embodiment, such compositions are pharmaceutical compositions. In one embodiment, the compound is a nucleic acid molecule encoding a 14-3-3 polypeptide (such as but not limited to those described in SEQ ID NOS: 1-6) or a 14-3-3 polypeptide derivative; such nucleic acid molecules may be delivered by the techniques known in the art or described herein. The compositions disclosed may comprise one or more of such compounds, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for administration, such compositions will contain an therapeutically effective amount of compound.

The pharmaceutical compositions of the disclosure may be used in the treatment and prevention methods of the present disclosure. Such compositions are administered to a subject in amounts sufficient to deliver a therapeutically effective amount of the compound(s) so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, and intramuscular. The compositions of the present disclosure may be administered only one time to the subject or more than one time to the subject. Furthermore, when the compositions are administered to the subject more than once, a variety of regimens may be used, such as, but not limited to, one per day, once per week, once per month or once per year. The compositions may also be administered to the subject more than one time per day. The therapeutically effective amount of the nucleic acid molecules and appropriate dosing regimens may be identified by routine testing in order to obtain optimal activity, while minimizing any potential side effects. In addition, co-administration or sequential administration of other agents may be desirable.

The compositions of the present disclosure may be administered systemically, such as by intravenous administration, or locally such as by subcutaneous injection or by application of a paste or cream.

The compositions of the present disclosure may further comprise agents which improve the solubility, half-life, absorption, etc. of the compound(s). Furthermore, the compositions of the present disclosure may further comprise agents that attenuate undesirable side effects and/or or decrease the toxicity of the compounds(s). Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions may further comprise a pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compound(s) of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compound(s) of the present disclosure may also be coupled with soluble polymers as targetable drug carriers. Such polymers can include, but are not limited to, polyvinylpyrrolidone, pyran copolymer, polyhydroxypropyl-methacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Results 14-3-3 RNA Expression is Altered in Transgenic Mice Overexpressing Wild-type α-syn In order to evaluate the role of 14-3-3 proteins in human disease, such as neurodegeneration, the expression of various 14-3-3 polypeptides was analyzed. In this study, a transgenic mouse model that over-expressed human wild-type α-syn under the control of the PDGFβ promoter was used. This model showed α-syn inclusions in several brain regions, particularly in the cortex (Masliah, E, et al., Science, 287:1265-69, 2000).

Figure 2:
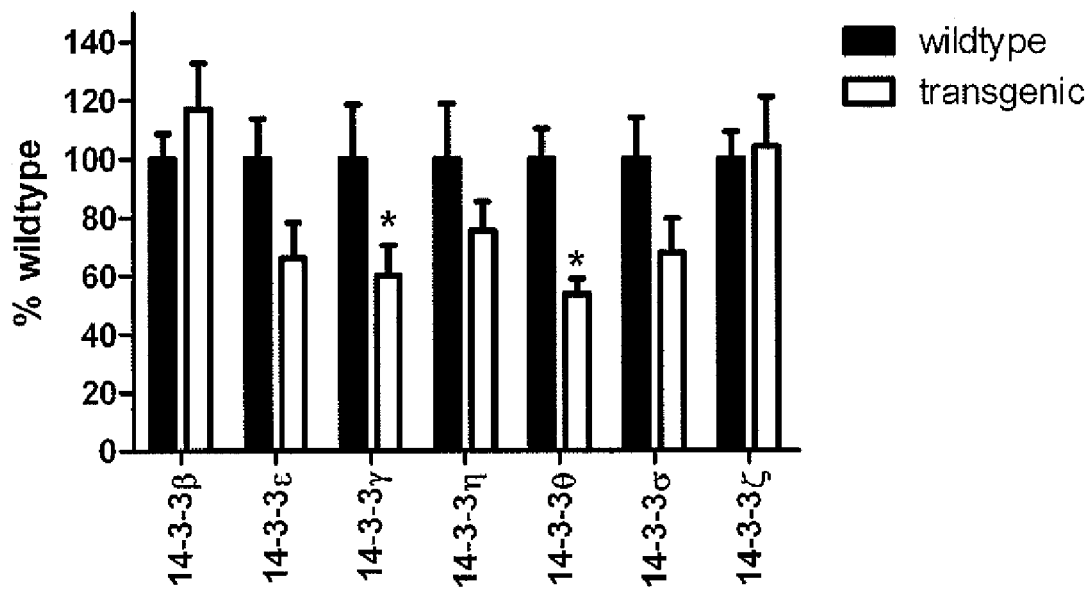
FIG. 2 shows 14-3-3 isoform RNA levels in the cortex of 3 month old α-syn transgenic (designated TG) and control (designated WT) littermates. RNA was extracted from the cortex of 3-month-old transgenic mice and wildtype littermates. Primers specific to each 14-3-3 isoform were used for quantitative PCR to determine the amount of each 14-3-3 transcript. Results were normalized to GAPDH. n=8 per group. *p<0.05 (Bonferroni's multiple comparison test).

Gene microarray studies revealed that the expression of several 14-3-3 isoforms was altered in the cortex of the transgenic mice (data not shown). To confirm this finding, the expression patterns of all seven isoforms were evaluated in the cortex of α-syn transgenic mice using quantitative real-time PCR. RNA was extracted from the cortex of 3-month-old α-syn transgenic mice (designated TG) and wildtype (designated TG) littermates. Primers specific to each 14-3-3 isoform were used for quantitative PCR to determine the amount of each 14-3-3 transcript. Results were normalized against GAPDH. The results are shown in FIG. 2. 14-3-3θ was the most significantly downregulated isoform in the cortex of the transgenic mice. This isoform was decreased by nearly 50% in transgenic mice as compared to wildtype mice (p value<0.05). 14-3-3γ was reduced to 60% of wildtype values (p<0.05). Expression of 14-3-3ε trended downward but did not reach statistical significance (p=0.072). Overall, expression levels of six of the seven isoforms were at similar levels in the control mice; 14-3-3σ was expressed at considerably lower levels in the cortex of control mice (data not shown). Therefore, FIG. 2 shows that the levels of the 14-3-3 γ, ε and θ isoforms were significantly down regulated in α-syn overexpressing transgenic mice, while 14-3-3 η, ζ and σ isoforms showed a less-significant or no down regulation. Interestingly, the 14-3-3 γ, ε, ζ, and θ isoforms are found in Lewy bodies in the brains of PD subjects (18).

Increasing Expression of 14-3-3 Polypeptide Reduces the Formation of α-syn Aggregates and Protects against α-syn Mediated Toxicity This data suggests that increasing 14-3-3 polypeptide levels could overcome the effects of α-syn overexpression. To evaluate this hypothesis the effect of increased 14-3-3 polypeptide expression on α-syn aggregation was evaluated.

Figure 3:
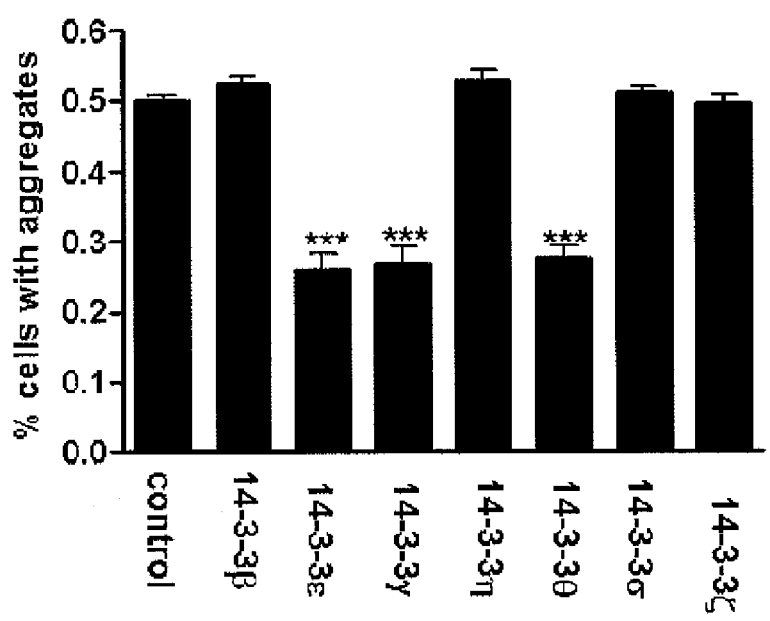
FIG. 3 shows the expression of 14-3-3 isoforms γ, ε and θ reduce α-syn aggregation in H4 cells. H4 cells were cotransfected with either empty vector or a 14-3-3 isoform along with synT and synphilin. 24 hours after transfection, cells were fixed and stained with a monoclonal antibody against α-syn. Cells that stained for α-syn were scored as positive or negative for α-syn aggregates, with the rater blind to experimental condition. Results reflect three independent experiments with four replicates per experiment. ***p<0.001 (Bonferroni's multiple comparison test).

In this experiment, the model of McLean et al., in which α-syn/green fluorescent protein (GFP) fusion protein (synT) forms visible aggregates in cells when expressed with synphilin (McLean, P J et al., Neuroscience, 104:901-12, 2001) was used. This system has been used to evaluate the effect of different polypeptides on α-syn aggregation (Kiucken, J., et al, J Biol Chem, 279:4625-31, 2004). Briefly, H4 cells were co-transfected with either empty vector or a vector containing nucleic acid encoding a 14-3-3 isoform, along with synT and synphilin. Twenty-four hours after transfection, cells were fixed and stained with a monoclonal antibody against α-syn. Results are shown in FIG. 3 and reflect three independent experiments with 4 replicates per experiment. FIG. 3 shows that increased levels of the 14-3-3 γ, ε and θ isoforms caused a 40% decrease (***$p<0.001$) in the number of H4 cells displaying α-syn aggregates. These are the same 14-3-3 isoforms that were decreased in α-syn transgenic mice (see FIG. 2). The remaining 14-3-3 isoforms showed no effect on α-syn aggregates.

Figure 4:
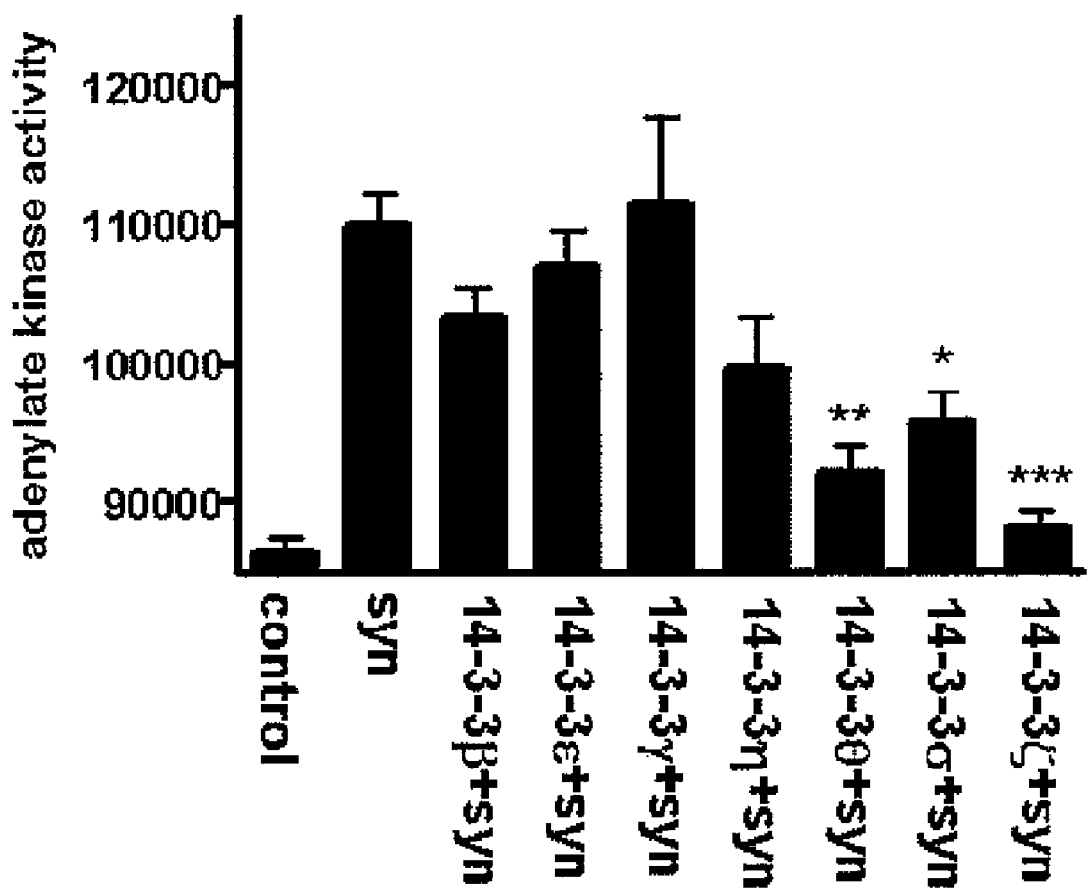
FIG. 4 shows the expression of 14-3-3 isoforms σ, ζ and θ reduce α-syn mediated toxicity in H4 cells. Briefly, H4 cells were transfected with wildtype α-syn and each of the 14-3-3 polypeptide isoforms or empty vector controls as discussed above. Twenty-four hours after transfection, cell death was assayed by adenylate kinase activity in the media (n=4, *p<0.05, p<0.01, *p<0.001).

To examine the neuroprotective properties of 14-3-3 polypeptides directly, H4 cells were used to determine if expression of 14-3-3 polypeptides resulted in reduced α-syn dependent cell death. Briefly, H4 cells were transfected with wildtype α-syn and each of the 14-3-3 polypeptide isoforms or empty vector controls as discussed above. Twenty-four hours after transfection, cell death was assayed by adenylate kinase activity in the media (n=4, *$p<0.05$, $p<0.01$, *$p<0.001$). This α-syn toxicity assay has been used previously to show the protective effects of members of the heat shock protein family (Klucken, J., et al, J Biol Chem, 279: 4625-31, 2004). The results are shown in FIG. 4. FIG. 4 shows that the 14-3-3 θ, ζ and σ isoforms exhibited protective effects.

Figure 5:
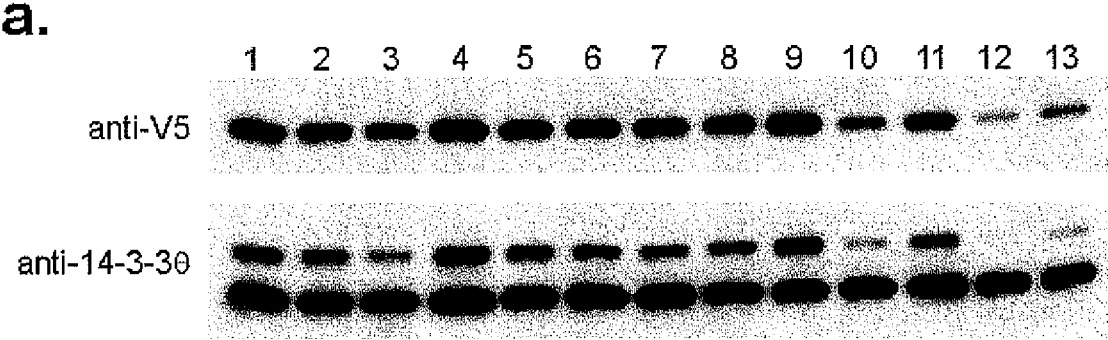
FIGS. 5A and B show a Western blot of stably transfected M17 cells expressing 14-3-3 isoforms.
FIG. 5B shows Western blots of stably transfected 14-3-3β, γ, ε, ζ, η and σ cells 15 to 20 stable clones for each of these 14-3-3 isoforms were created as described above and analyzed for 14-3-3 overexpression by Western blot against the V5 epitope tag. Two to three clones for each 14-3-3 isoform were selected for further experiments based on high expression levels. Western blots of these selected clones are shown using an monoclonal antibody against V5 to detect exogenous 14-3-3 isoforms as indicated.
Figure 5:
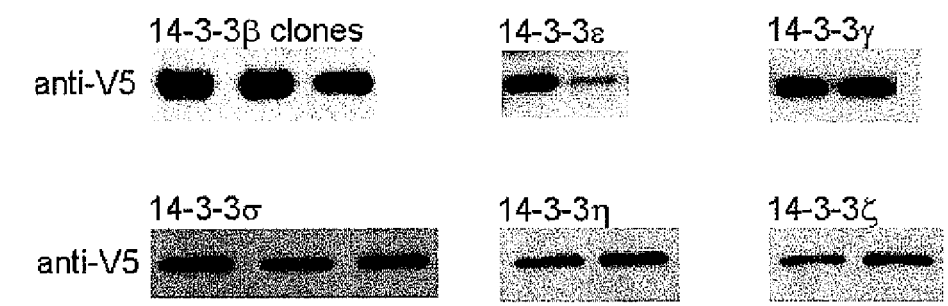

Additional studies were conducted to evaluate the effect of difopein, a competitive ligand inhibitor of 14-3-3 polypeptides (Masters, S C, et al, J Biol Chem, 276.45193-200, 2001), on rotenone toxicity in the dopaminergic cell line SH-SY5Y. Briefly, cells were transfected with vectors encoding difopein-EYFP. Twenty-four hours after transfection, cells were treated with rotenone for 24 hours at the same concentrations used in FIG. 5. Cells were evaluated as described in relation to FIG. 5. Difopein caused increased apoptosis at baseline. The addition of rotenone showed further increases in apoptosis in a dose-dependent manner.

Stable Cell Lines Overexpressing 14-3-3θ are Resistant to the Neurotoxin Rotenone The data above provide support for the role of 14-3-3 polypeptides in preventing neurodegeneration. In particular, the 14-3-3 θ isoform exhibited protective effects in all model systems tested. The above data suggests that increased 14-3-3 polypeptide activity, such as via augmentation of 14-3-3 polypeptide expression, will be protective against neurodegeneration and is viable in treatment and prevention methods of disease states that are characterized, at least in part, by neurodegeneration.

Additional studies were performed to evaluate the effect of 14-3-3 polypeptide isoforms in mammalian cells. In these studies, cDNA clones for the 14-3-3 polypeptide β, γ, ε, η, θ, and σ isoforms were subcloned into the mammalian expression vector pcDNA 3.1/V5/His (Invitrogen). The polypeptide expressed from this vector contains the particular 14-3-3 isoform with a V5 and a $His_6$ tag at the C-terminal end. The V5 and $His_6$ tags allows direct immunohistochemical and biochemical results to be attributed to a particular isoform and offer advantages over antibodies to the isoforms themselves since the isoforms share such a great sequence homology with one another. SK-N-BE(2)-M17 (M17) cells, a dopaminergic-producing human neuroblastoma cell line, were transfected with each isoform or empty vector using Superfect, and stably-transfected cells were selected for in the presence of G418.

Approximately 15 to 20 clones for each 14-3-3 isoform were created. Clones overexpressing 14-3-3θ expressed that isoform at varying levels as determined by Western blotting (FIG. 5A). The top panel shows the immunoblot against the V5 epitope tag, while the bottom panel shows an immunoblot against 14-3-3 θ, where the top band represent exogenous 14-3-3θ and the bottom band represent endogenous 14-3-3θ. Similarly, clones overexpressing the other 14-3-3 isoforms expressed the given 14-3-3 isoform at varying levels (FIG. 5B). The two to three highest-expressing clones were chosen for the experiments described below. A control stable line was created by transfecting M17 cells with the empty pcDNA3.1/V5-His plasmid.

Overexpression of 14-3-3 isoforms in these stably-transfected lines did not appear to affect the cellular distribution of 14-3-3s. Immunostaining of naïve M17 cells with an antibody against 14-3-3ε revealed predominantly cytoplasmic distribution. A similar cellular distribution is seen when 14-3-3ε-overexpressing stable cells were immunostained with an antibody against the V5 epitope tag. This V5 antibody detects only the exogenous and not the endogenous 14-3-3ε in these stable cells (data not shown).

14-3-3 Overexpression Reduces Rotenone Toxicity

Figure 6:
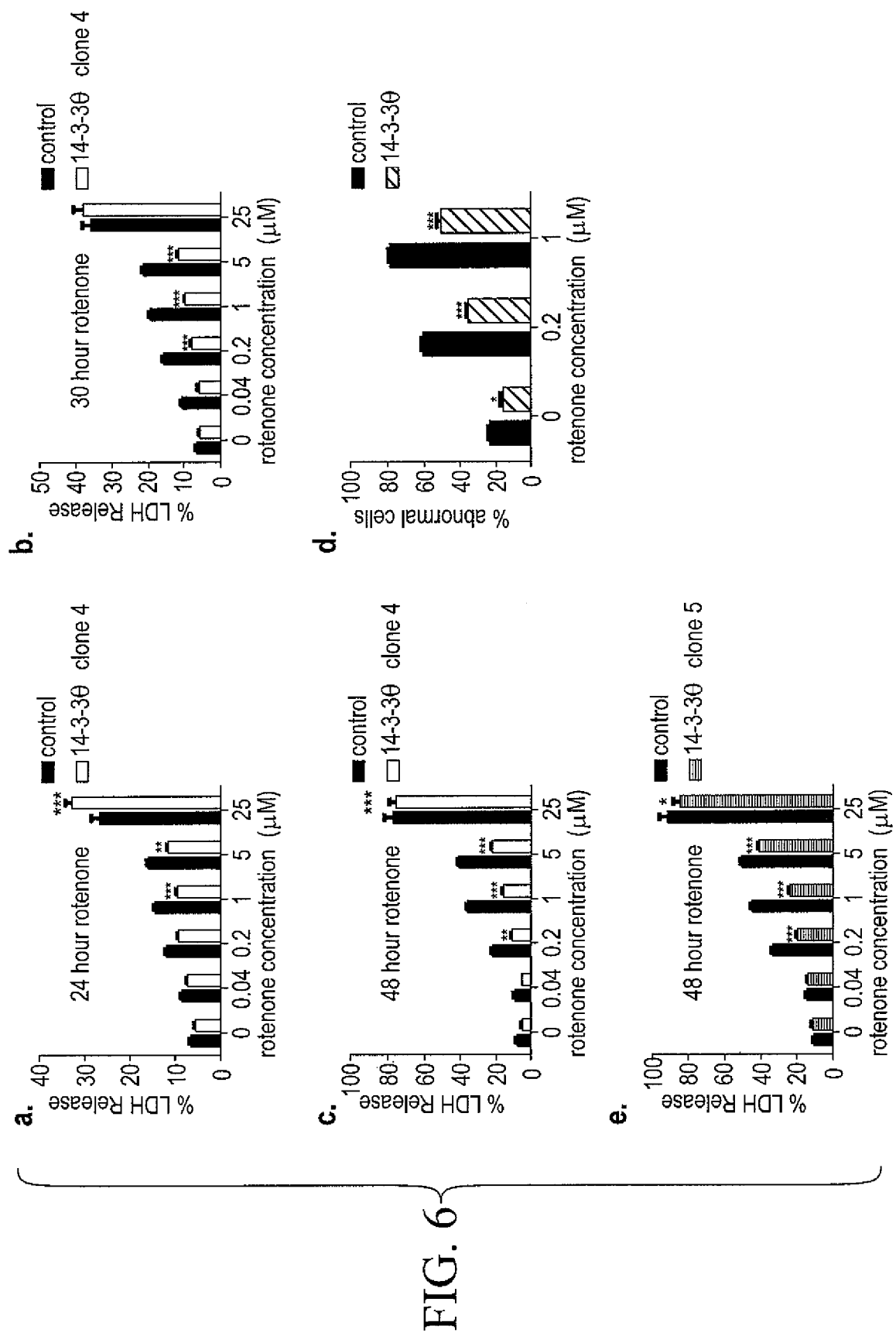
FIGS. 6A-D show M17 cells overexpressing 14-3-3θ are resistant to rotenone treatment. Cell lines stably-transfected with either 14-3-3θ or empty vector were treated with varying concentrations of rotenone (0-25 μM) for 24 hours (FIG. 6A), 30 hours (FIG. 6B), or 48 hours (FIG. 6C). Cell death was assayed by LDH release into the culture media. LDH release into media was normalized to total LDH release for each well. The 14-3-3θ-overexpressing line was more resistant to rotenone in a dose-dependent manner compared to control stable cells at all time points tested. At the 48 hour time point, a second 14-3-3θ-overexpressing stable clone was tested to verify these results (bottom graph in FIG. 6C). Results reflect two to three independent experiments with at least two replicates per experiment. *p<0.05, p<0.01, *p<0.001 (Bonferroni's multiple comparison test.

Rotenone is a pesticide that has been shown to induce a Parkinsonian syndrome in animals (Sherer, T B, et al., J. Neurosci, 23:10756-64, 2003) and reliably produces dose-dependent injury to dopaminergic cell lines (Betarbet, R. et al, Nat Neurosci, 3:1301-06, 2000). The M17 14-3-3θ clones were examined for their resistance to rotenone (0-25 µM). M17 cell lines stably transfected with either 14-3-3θ or empty vector were treated with rotenone for 24 (FIG. 6A), 30 (FIG. 6B) or 48 hours (FIG. 6C). Cell death was assayed by lactose dehydrogenase (LDH) release into the culture media using the LDH assay kit from Roche. LDH release into media was normalized to total LDH release for each well. Results reflect three independent experiments with at least two replicates per experiment. As shown in FIGS. 6A-C, 14-3-3θ expressing cells were more resistant to rotenone toxicity as compared to control cells at all time points that we tested. The difference between control and 14-3-3θ cells was most prominent at 48 hours. 48 hours after 1 µM rotenone treatment, cell death in response to 1 µM rotenone in the 14-3-3θ was reduced to 45% of that in control cells (FIG. 6C). Two separate clones overexpressing 14-3-3θ were tested at the 48 hour time point with similar results (bottom panel, FIG. 6C). Protection against rotenone was dose-dependent. Mild protection against rotenone was seen at 0.04 and 0.2 µM doses and more prominent protection was apparent at 1 and 5 µM doses.

The effects of 14-3-3θ overexpression on rotenone toxicity was also examined by transient transfection of this isoform into naïve M17 cells. Briefly, M17 cells were transfected with V5-tagged 14-3-3θ isoform or enhanced yellow fluorescent protein (EYFP) (control) and were treated with rotenone for 24 hours at 0, 0.2, or 1 µM rotenone. Because of the relatively low rates of transfection, after the treatment period cells were fixed and stained against V5 (or GFP in the case of control), followed by Hoechsht 33342 staining. With the rater blind to experimental condition, the nuclei of cells that stained for V5 or GFP were scored as normal or apoptotic. Once again, 14-3-3θ-overexpressing cells showed decreased cell death in response to rotenone treatment (FIG. 6D).

Knockdown of 14-3-3θ does not Promote Rotenone Toxicity

Next, it was examined whether reduction of 14-3-3θ levels would result in increased toxicity of M17 cells to rotenone. Four different lentiviral shRNAs that target 14-3-3θ were tested for their ability to reduce 14-3-3θ expression. M17 cells were infected with lentivirus containing the lentiviral construct pLKO.1 with a shRNA directed against 14-3-3θ. For control, M17 cells were infected with lentivirus containing the empty pLKO.1 lentiviral vector. Infected cells were selected for in the presence of puromycin. All four 14-3-3θ shRNA lentiviruses were able to significantly reduce 14-3-3θ expression in M17 cells as compared to control virus, tubulin expression was not impacted (FIG. 7A). Control and 14-3-3θ knockdown cells were incubated with varying concentrations of rotenone (0-25 µM) in serum-free DMEM for 48 hours, and cell death was assayed by LDH release into the culture media. Those cells in which 14-3-3θ levels were reduced showed equivalent rotenone toxicity as compared to control cells (FIG. 7B). These results were confirmed using a second 14-3-3θ shRNA in the same lentiviral construct (data not shown).

Differential Effects of Overexpression of 14-3-3 Isoforms on Rotenone Toxicity

Figure 7:
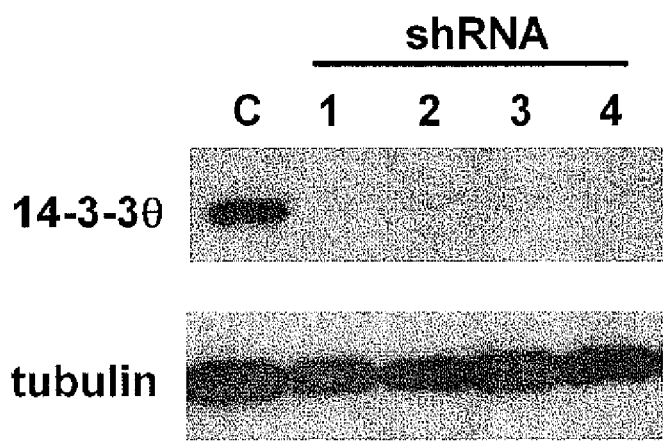
FIGS. 7A and B show knockdown of 14-3-3 expression does not promote rotenone toxicity.
FIG. 7B shows 14-3-3θ knockdown cells incubated with varying concentrations of rotenone. Cell death was assayed by LDH release into the culture media. Control (C) or 14-3-3θ-shRNA cells (shRNA 1 from blot) were treated with rotenone at varying concentrations (0-25 μM) in serum-free DMEM for 48 hours. No considerable difference was seen between control cells and 14-3-3θ knockdown cells. Results reflect three independent experiments with 2 replicates per experiment. *p<0.05 (Bonferroni's multiple comparison test).
Figure 7:
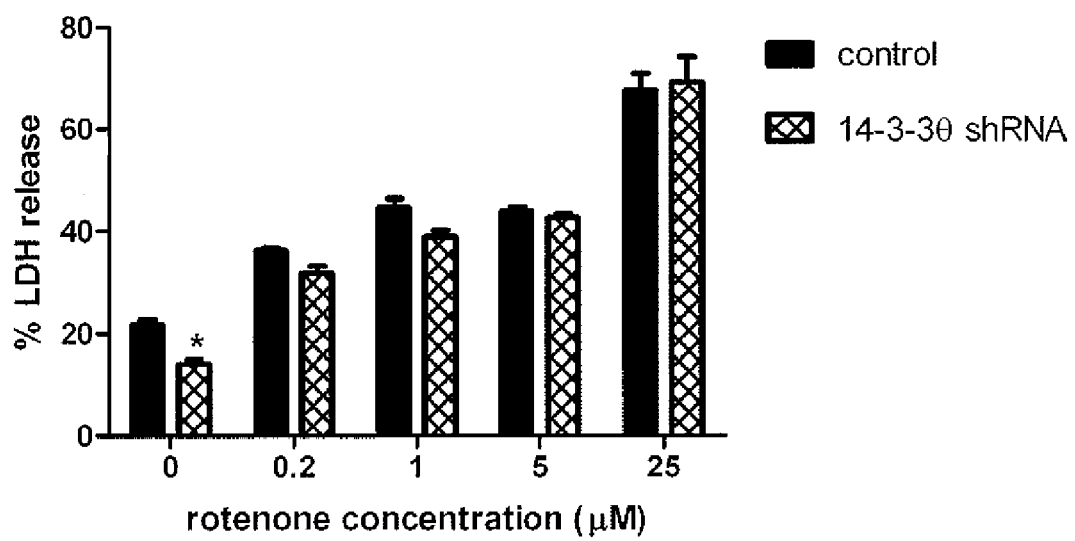
Figure 8:
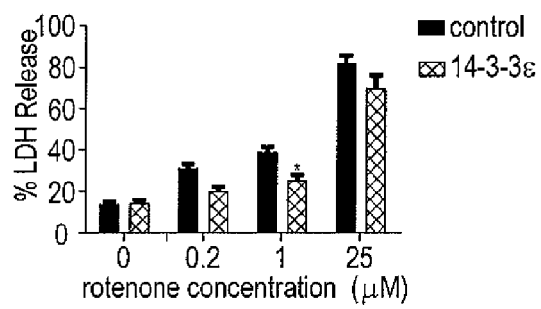
FIGS. 8A-F show differential effects of overexpression of 14-3-3β, γ, ζ, η and σ isoforms on rotenone toxicity. M17 cell lines stably-transfected with either a 14-3-3 isoform or empty vector were treated with varying concentrations of rotenone (0-25 μM) for 48 hours. Cell death was assayed by LDH release into the culture media. LDH release into media was normalized to total LDH release for each well. Lines overexpressing 14-3-3ε (FIG. 8A), 14-3-3γ (FIG. 8B), 14-3-3β (FIG. 8C), 14-3-3 ζ (FIG. 8D), 14-3-3 η (FIG. 8E) and 14-3-3σ (FIG. 8F) are shown. Results reflect two to three independent experiments with at least two replicates per experiment. *p<0.05, p<0.01, *p<0.001 (Bonferroni's multiple comparison test).
Figure 8:
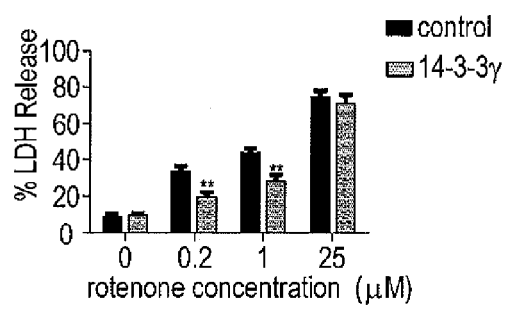
Figure 8:
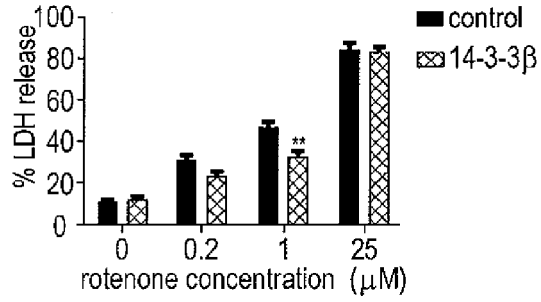
Figure 8:
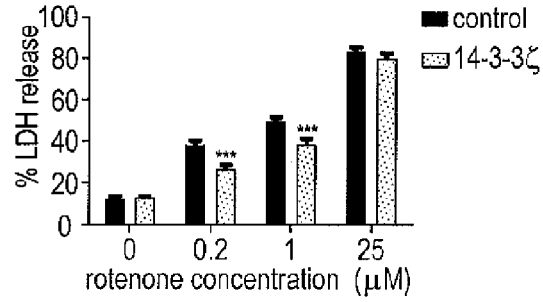
Figure 8:
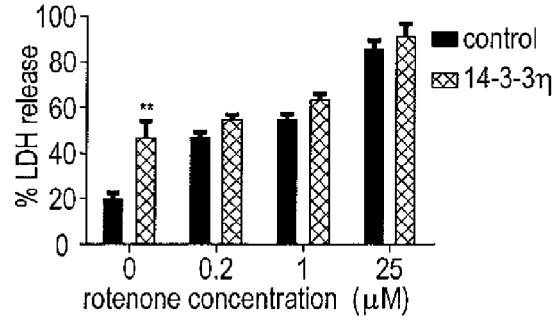
Figure 8:
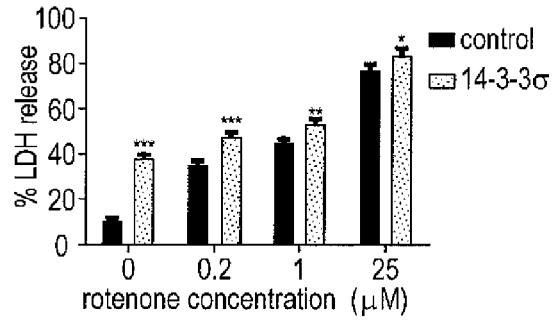

Given the results above, the effect of overexpression of other 14-3-3 isoforms was also tested to determine if the other 14-3-3 isoforms could also protect against rotenone toxicity. Stable M17 cell lines overexpressing these other isoforms were treated with rotenone at varying concentrations, and then cell death was assayed at 48 hours by LDH release. Significant differences between the different isoforms in terms of their ability to protect against rotenone were observed. Cells overexpressing 14-3-3ε and γ isoforms showed prominent reduction in rotenone-induced toxicity in a dose-dependent manner (FIGS. 8A and B). Rotenone-induced cell death at 1 µM was reduced to 65% and to 55% of control levels in the 14-3-3ε and 14-3-3γ lines, respectively. Overexpression of 14-3-3β and ζ also provided some protection, but perhaps not to the same extent as 14-3-3θ, ε and γ (FIGS. 8 C and D). Rotenone-induced cell death at 1 µM was reduced to 75% and 78% of control levels in 14-3-3β cells and 14-3-3ζ cells, respectively. Differences in protection do not seem to correlate with 14-3-3 expression levels, as 14-3-3β cells appear to have higher V5 staining on Western blots compared to 14-3-3θ and ε but show less protection (FIG. 7). The results for each isoform were confirmed in one to two other cell clones overexpressing that isoform (data not shown).

Cells overexpressing 14-3-3η or σ did not provide any protection against rotenone toxicity at any of the doses tested (FIGS. 8E and F). Instead, 14-3-3η and σ cells showed increased cell death, as assayed by LDH release, when maintained serum-free media compared to control cells. In the presence of rotenone, the 14-3-3σ cells continued to show increased toxicity compared to control, although the difference between 14-3-3σ and control cells was less prominent. The 14-3-3η cells showed a non-significant trend towards increased toxicity in the presence of rotenone compared to control cells. These findings suggest that the 14-3-3η and σ cells were more sensitive to serum deprivation per se instead of rotenone, but overexpression of neither isoform reduced rotenone toxicity as the other 14-3-3 isoforms did. The results for 14-3-3η and σ were confirmed in one to two other cell clones overexpressing that isoform (data not shown).

Stable Cell Lines Overexpressing 14-3-3θ Show Delayed Toxicity in Response to the Neurotoxin MPP+

The 14-3-3 expressing M17 clones were also tested for resistance to the neurotoxin 1-methyl-4-phenylpyridinium ion (MPP+), which is a metabolite of 1-methyl-4-phenyl-1,2,3,6-tetrahydropyridine (MPTP). M17 cells expressing the 14-3-3 isoforms were prepared as described. M17 cells were treated with MPP+ (0-10 mM) for 24 hours (FIGS. 9A-G). Cell death was assayed by LDH release into the culture media as described above.

Figure 9:
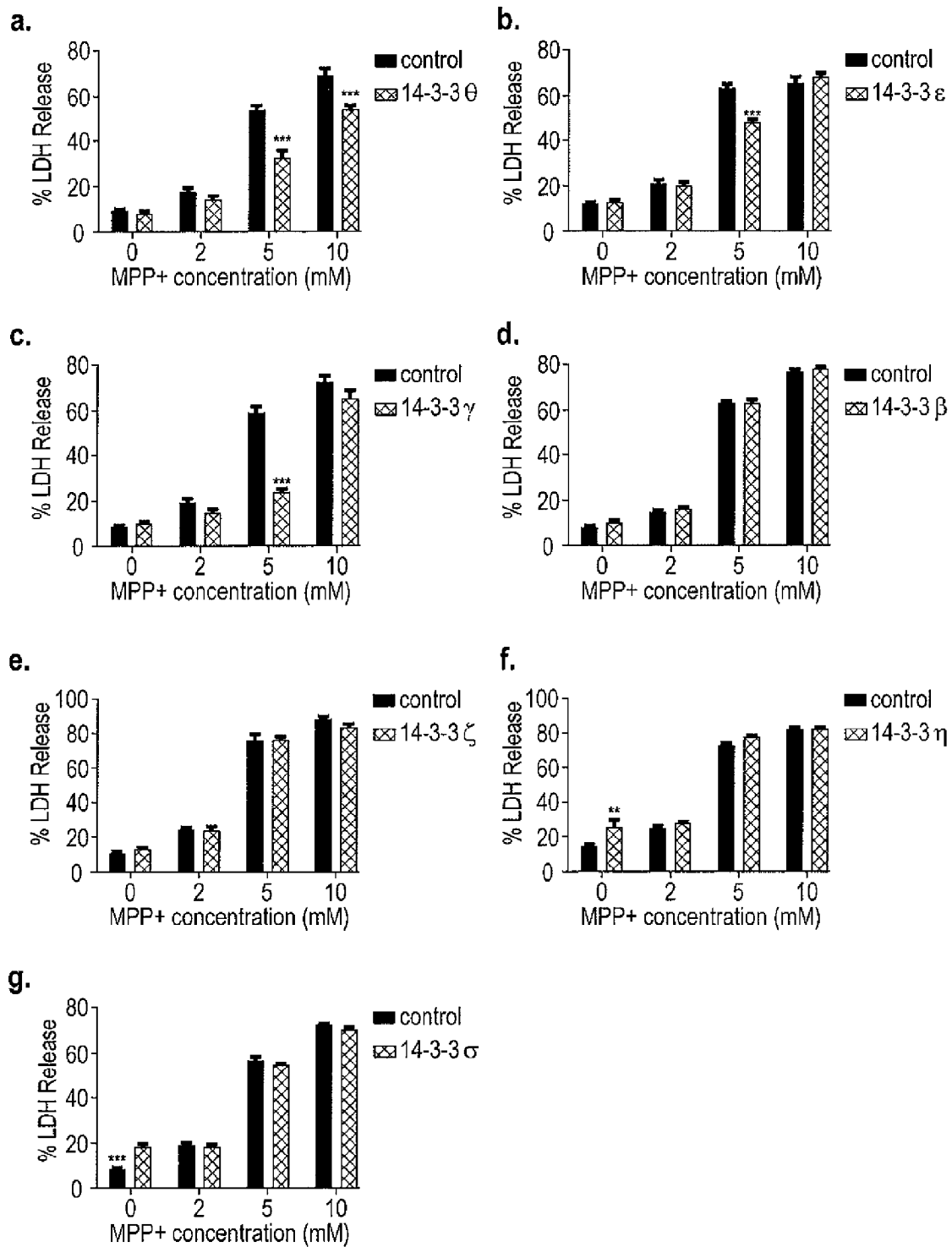
FIGS. 9A-G show stably transfected M17 cells overexpressing 14-3-3θ, γ and ε overexpression reduced toxicity in response to MPP+ treatment in a dose-dependent manner at 24 hours. Cell lines stably-transfected with either a 14-3-3 isoform or empty vector were treated with varying concentrations of MPP+ for 24 hours. Cell death was assayed by LDH release into the culture media. LDH release into media was normalized to total LDH release for each well. Lines overexpressing 14-3-3θ (FIG. 9A), 14-3-3ε (FIG. 9B), or 14-3-3γ (FIG. 9C) were more resistant to MPP+ in a dose-dependent manner compared to control stable cells. In contrast, overexpression of 14-3-3β (FIG. 9D), 14-3-3ζ (FIG. 9E), 14-3-3η (FIG. 9F), or 14-3-3σ (FIG. 9G) did not protect against MPP+. Results reflect two to three independent experiments with at least two replicates per experiment. p<0.01, *p<0.001 (Bonferroni's multiple comparison test).

Consistent with previous results, 14-3-3θ, γ and ε overexpression reduced toxicity in response to MPP+ treatment in a dose-dependent manner (FIGS. 9A-C). In contrast to the effects on rotenone toxicity, 14-3-3β and ζ overexpression did not show any significant protection against MPP+ treatment at any of the doses tested (FIGS. 9D and E). 14-3-3η and σ cells also showed similar levels of cell death compared to control cells in response to MPP+ treatment (FIGS. 9F and G). Once again, these two sets of lines showed increased toxicity compared to control cells in serum-free media in the absence of MPP+, as was seen in the rotenone experiments.

14-3-3s' Effects on α-syn Toxicity

Figure 10:
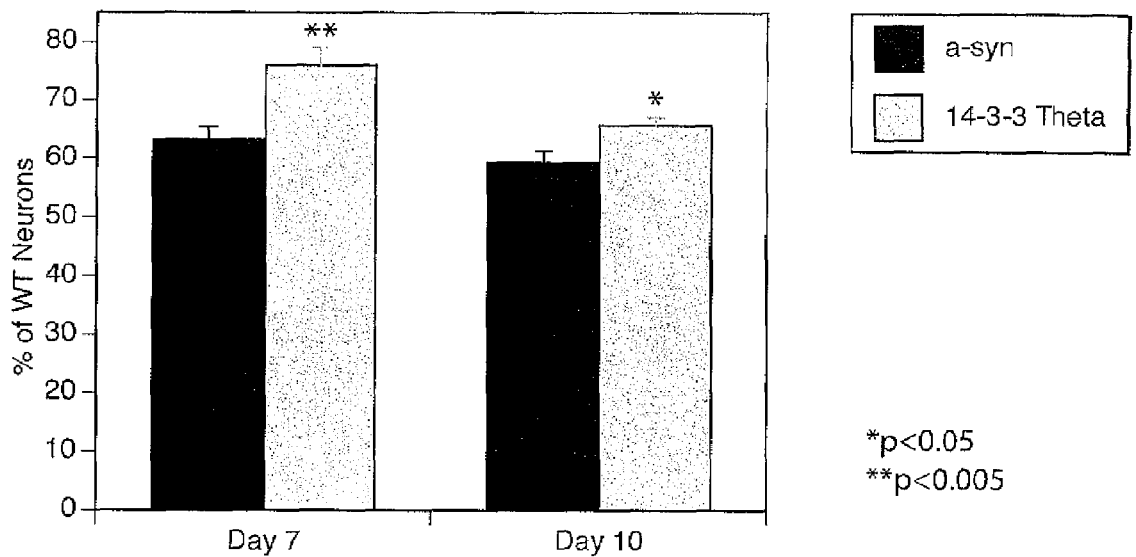
FIG. 10. Overexpression of 14-3-3θ protects against dopaminergic cell loss in the α-syn transgenic C. elegans worm model. Double transgenic worms were created in which the 14-3-3θ isoform was overexpressed along with α-syn.

While both rotenone and MPP+ have been both described as inducing α-syn aggregation, we wished to assess more directly the potential protective effects of 14-3-3s against α-syn toxicity. We turned to the C. elegans model of PD, in which human wildtype α-syn is overexpressed. Transgenic C. elegans worms that overexpress human wildtype α-syn demonstrate a predictable loss of dopaminergic neurons. Double transgenic worms were created in which the 14-3-3θ isoform was overexpressed along with α-syn. In control worms that overexpressed only α-syn, we found that only 9.4% of worms had all six anterior dopaminergic neurons present at seven days, and this percentage dropped to 5.0% at ten days (FIG. 10). In contrast, 18.9% of worms that overexpressed human 14-3-3θ along with α-syn had all six dopaminergic neurons at seven days (FIG. 10; p<0.001 compared to α-syn worms). 12.9% of worms had the full anterior complement of dopaminergic neurons at 10 days (FIG. 10; p<0.00001).

Summary

The results presented show that RNA levels of 14-3-3ε, γ, and θ isoforms are reduced in transgenic mice overexpressing human α-syn. Furthermore, the increased expression of 14-3-3ε, γ, and θ isoforms reduced α-syn aggregation in H4 cells and reduced toxicity in response to the neurotoxins rotenone and MPP+. Furthermore, 14-3-3θ prevented dopaminergic neuron loss in a C. elegans model.

Figure 11:
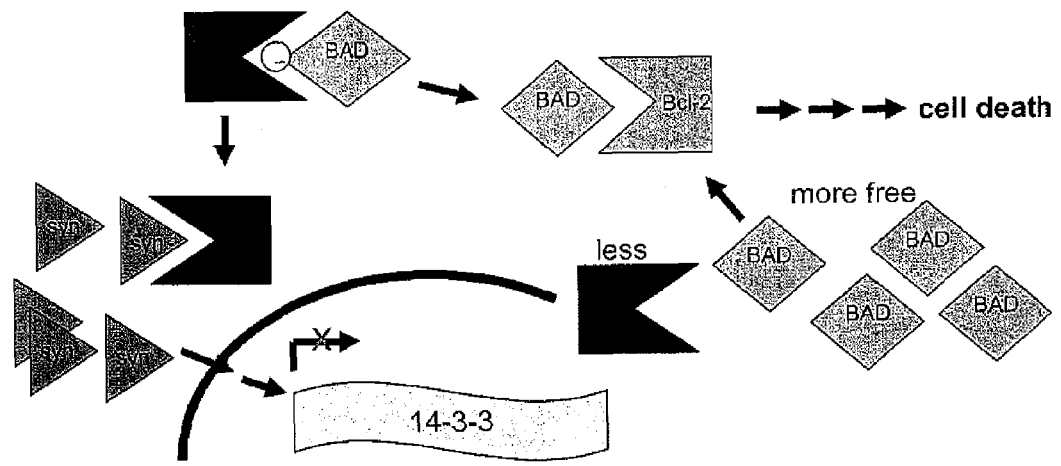
FIG. 11 shows an exemplary mechanism of 14-3-3 polypeptide activity.

FIG. 11 shows one potential model for the 14-3-3 polypeptide activity and how inhibition of such 14-3-3 polypeptide activity could contribute to neurodegeneration. In FIG. 11, a 14-3-3 polypeptide displays a 14-3-3 polypeptide activity, illustrated in this embodiment as binding to phosphorylated BAD protein (BAD is an illustrative binding partner; other 14-3-3 binding partners may be substituted for BAD). BAD protein interacts with Bcl-2 and contributes to cell death via apoptosis. The 14-3-3 polypeptide through binding to BAD prevents the BAD/Bcl-2 interaction, thereby inhibiting apoptosis. This 14-3-3 polypeptide activity is disrupted by α-syn, which interacts with the 14-3-3 polypeptide, resulting in the release of BAD and allowing its interaction with Bcl-2 and stimulation of apoptosis. When α-syn, a protein correlated with neurodegeneration and neurodegenerative disorders such as PD, is overexpressed, cellular apoptosis can occur with the resulting neurodegeneration through neuronal cell loss. In addition, the PCR data from α-syn transgenic mice indicated that elevated α-syn levels lead to decreased transcription of 14-3-3 polypeptide, resulting in decreased 14-3-3 polypeptide expression. This decrease in expression accentuates the loss of 14-3-3 polypeptide activity resulting from the interaction with excess α-syn. Increasing the expression of a 14-3-3 polypeptide, such as the isoform, can alleviate the effects of α-syn overexpression and reinstate normal 14-3-3 polypeptide activity, resulting again in 14-3-3/BAD binding and a decrease in apoptosis.

These results support a role for 14-3-3 polypeptides in the mechanisms of neurodegeneration and provides for novels methods of treating and preventing disease states that are characterized, at least in part, by decreased 14-3-3 polypeptide activity (such as neurodegeneration) by increasing a 14-3-3 polypeptide activity.

Methods

Animals α-syn transgenic mice originally generated by Masliah et al. were bred at Charles River Laboratories to generate transgenic and wildtype littermates. The use of mice was supervised by the Massachusetts General Hospital Animal Resources Program in accordance with the PHS policy on Humane Care and Use of Laboratory Animals. Mice were euthanized by $CO_2$ inhalation. Gender-matched wildtype and transgenic mice were sacrificed at three months of age.

Quantitative PCR 20mer, synthetic PCR primers specific to each 14-3-3 isoform were designed using Primer3. RNA was extracted from mouse cortex and reverse transcribed into first-strand cDNA using SuperScript™ II reverse transcriptase kit (Invitrogen). First strand cDNA was incubated with primers and SYBR® Green PCR Master Mix (Applied Biosystems) in a 96-well plate. QPCR was performed using an iQ5Cycler (BioRad) set to the following protocol: 1 cycle of denaturation at 95° C. for 10 min; 50 cycles of denaturation at 95° C. for 30 sec, annealing at 57° C. for 30 sec, and polymerization at 72° C. for 45 sec; and 80 0.5° C. increases in temperature to collect melting curve data. We used a standard curve with known concentrations of cDNA to calculate primer efficiency and to quantitate PCR products. Quantity of each PCR sample was calculated by the ΔΔCt method.

Primers against each of the human 14-3-3 isoforms were designed using Primer3. Primers against 14-3-3β (NM_018753) were 5' aaaggtcccgtgctcatacc 3' (forward; SEQ ID NO. 9) and 5' gccgcctcaacacattattc 3' (reverse; SEQ ID NO. 10). Primers against 14-3-3ε (NM_009536) were 5' ttgggt-gttagcttgaggtg 3' (forward; SEQ ID NO. 11) and 5' gag-gagtcggcaagaatgag 3' (reverse; SEQ ID NO. 12). Primers against 14-3-3γ (NM_018871) were 5' tctgtgtcccgcttgtactg 3' (forward; SEQ ID NO. 13) and 5' aggcaggcacacttctcaac 3' (reverse; SEQ ID NO. 14). Primers against 14-3-3η (NM_011738) were 5' tctagcaaatccaggtgatgg 3' (forward; SEQ ID NO. 15) and 5' aggctgatggtgaaggaatg 3' (reverse; SEQ ID NO. 16). Primers against 14-3-3θ (NM_011739) were 5' aggagt-gacagcacacttgg 3' (forward; SEQ ID NO. 17) and 5' gttgct-tctgaaaggaaacctc 3' (reverse; SEQ ID NO. 18). Primers against 14-3-3σ (NM_018754) were 5' gtctgtccttcatcgcagtc 3' (forward; SEQ ID NO. 19) and 5' tcctcgttgctcttctgctc 3' (reverse; SEQ ID NO. 20). Primers against 14-3-3ζ(NM_011740) were 5' ggctagtgattggaggaaacc 3' (forward; SEQ ID NO. 21) and 5' tcatatcgctctgcctgctc 3' (reverse; SEQ ID NO. 22). Primers against GAPDH were 5' tggtgaagcaggeatctga 3' (forward; SEQ ID NO. 23) and 5' tgctgttgaagtcgcaggag 3' (reverse; SEQ ID NO. 24) and were used to normalize PCR results.

α-syn aggregation assay H4 cells were transfected with synphilin, α-syn/green fluorescent protein (synT), and either empty vector control or a 14-3-3 isoform using Superfect transfection reagent (Qiagen). 24 hours after transfection, cells were fixed with 4% paraformaldehyde and immunostained with a monoclonal antibody against α-syn (BD Transduction) and a secondary Alexa 488-conjugated goat anti-mouse antibody (Molecular Probes). All cells stained for α-syn were scored as positive or negative for α-syn aggregates, with the rater blind to experimental condition.

α-syn toxicity assay H4 cells were transfected with α-syn and either empty vector control or a 14-3-3 isoform using Superfect transfection reagent (Qiagen). 24 hours after transfection, toxicity was measured by the amount of adenylate kinase released into the media using the ToxiLight™ kit (Cambrex).

Creation of stable cell lines Each 14-3-3 isoform was subcloned into the mammalian expression vector mcDNA3.1/V5-His (Invitrogen). BE(2)-M17 cells were transfected with each isoform or empty vector using Superfect, and stably-transfected cells were selected for in the presence of G418. About 15-20 clones for each isoform were selected for evaluation of 14-3-3 expression by Western blotting.

Immunoblotting Cells were sonicated for 10 seconds on ice in lysis buffer (150 mM NaCl, 10 mM Tris-HCl, pH 7.4, 1 mM EGTA, 1 mM EDTA, 0.5% NP-40, protease inhibitor cocktail (Roche)) and centrifuged at 16000 g for 10 minutes. Protein concentrations of supernatants were determined by the bicinchoninic acid assay (BCA; Pierce, Rockford, Ill.). Samples were boiled for 5 minutes in 4×DTT sample loading buffer (0.25 M Tris-HCl, pH 6.8, 8% SDS, 200 mM DTT, 30% glycerol, bromophenol blue), resolved on 15% SDS-polyacrylamide gels, and transferred to PVDF membranes. Blots were blocked in 5% non-fat dry mild in TBST (25 mM Tris-HCl, pH 7.6, 137 mM NaCl, 0.1% Tween-20) for one hour, and then incubated with primary mouse monoclonal antibody against V5 (1:5000; Invitrogen) or against 14-3-3 proteins as indicated (1:10000; Abcam). After three washes in TBST, blots were incubated with HRP-conjugated goat anti-mouse secondary antibody for 2 hours and then washed in TBST six times for 10 minutes. Blots were developed with the enhanced chemiluminescence method.

Immunocytochemistry Naïve M17 cells and certain 14-3-3-overexpressing stable cell clones were fixed in 4% paraformaldehyde and permeabilized with Triton X-100. After incubation with 1% normal goat serum, cells were incubated overnight at 4° C. with a mouse monoclonal antibody against the V5 epitope tag (Invitrogen), a rabbit polyclonal antibody against 14-3-3ε (Abcam), or a mouse monoclonal antibody against 14-3-3θ (Abeam). Following washes in TBS, cells were incubated with cy-3-conjugated goat anti-mouse or anti-rabbit secondary antibody for 2 hours at room temperature.

LDH assay Empty vector control and 14-3-3 stable lines were treated with varying concentrations of rotenone and MPP+ for 24 or 48 hours. Toxicity was assayed by LDH release into media using the LDH assay kit from Roche. LDH release into media was normalized to total LDH release for each well.

RNA interference 14-3-3θ shRNA pLKO.1 lentiviral constructs created by The RNA Consortium were purchased from Open Biosystems (Huntsville, Ala.). Packaging of lentiviral shRNA constructs was done by the UAB Neuroscience NINDS Protein Core (P30 NS47466). All five shRNA constructs were tested for their efficacy in reducing 14-3-3θ protein expression, and two constructs were chosen for use in the rotenone toxicity experiments. M17 cells were infected with the empty vector pLKO.1 virus or one of the two 14-3θ shRNA-containing pLKO.1 viruses. 72 hours after infection, infected cells were selected for in the presence of puromycin. Selected cells were used for rotenone (and MPP+) toxicity experiments as described under LDH assay.

The foregoing description illustrates and describes the methods and other teachings of the present disclosure. Additionally, the disclosure shows and describes only certain embodiments of the methods and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the methods and other teachings of the present disclosure are not intended to limit the exact embodiments and examples disclosed herein. All references cited herein are incorporated by reference as if fully set forth in this disclosure.

What is claimed:

1. A method diagnosing a subject as suffering from or at risk for Parkinson's disease, said method comprising:
   (a) determining a level of expression of a 14-3-3θ isoform in a sample of the cortical tissue of the subject;
   (b) comparing said level of expression to a control sample taken from a subject that is determined not to be suffering from Parkinson's disease; and
   (c) diagnosing the subject as suffering from or at risk of Parkinson's disease if the level of expression of the θ isoform is below the level of expression of the control sample.

* * * * *

UNITED STATES PATENT AND TRADEMARK OFFICE
CERTIFICATE OF CORRECTION

PATENT NO. : 7,919,262 B2
APPLICATION NO. : 12/267337
DATED : April 5, 2011
INVENTOR(S) : Yacoubian et al.

Page 1 of 1

It is certified that error appears in the above-identified patent and that said Letters Patent is hereby corrected as shown below:

In the Specification

Column 1, Line 14, add:
Statement Regarding Federally Sponsored Research or Development
This invention was made with government support under grant number NS060948 awarded by the National Institutes of Health. The government has certain rights in the invention.

Signed and Sealed this
Twenty-first Day of April, 2020

Andrei Iancu
*Director of the United States Patent and Trademark Office*